(12) United States Patent
Grauert et al.

(10) Patent No.: US 7,700,769 B2
(45) Date of Patent: Apr. 20, 2010

(54) DIHYDROPTERIDIONE DERIVATIVES, PROCESS FOR THEIR MANUFACTURE AND THEIR USE AS MEDICAMENT

(75) Inventors: Matthias Grauert, Biberach (DE); Matthias Hoffmann, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 132 days.

(21) Appl. No.: 12/192,499

(22) Filed: Aug. 15, 2008

(65) Prior Publication Data

US 2009/0018333 A1 Jan. 15, 2009

Related U.S. Application Data

(62) Division of application No. 11/210,379, filed on Aug. 24, 2005, now Pat. No. 7,414,053.

(30) Foreign Application Priority Data

Aug. 25, 2004 (EP) .................................. 04020124

(51) Int. Cl.
C07D 295/116 (2006.01)
(52) U.S. Cl. ...................................... 544/175
(58) Field of Classification Search .................. 544/175
See application file for complete search history.

(56) References Cited

U.S. PATENT DOCUMENTS

| | | | |
|---|---|---|---|
| 4,957,922 A | 9/1990 | Lammens et al. |
| 5,167,949 A | 12/1992 | Ferrand et al. |
| 5,424,311 A | 6/1995 | Billhardt-Troughton et al. |
| 5,698,556 A | 12/1997 | Chan |
| 6,096,924 A | 8/2000 | Studer et al. |
| 6,174,895 B1 | 1/2001 | Kleinman |
| 6,605,255 B2 | 8/2003 | Kroll et al. |
| 6,806,272 B2 | 10/2004 | Bauer et al. |
| 6,861,422 B2 | 3/2005 | Hoffmann et al. |
| 7,238,807 B2 | 7/2007 | Duran et al. |
| 7,241,889 B2 | 7/2007 | Hoffmann et al. |
| 7,332,491 B2 | 2/2008 | Grauert et al. |
| 7,371,753 B2 | 5/2008 | Stadtmueller et al. |
| 7,414,053 B2 | 8/2008 | Grauert et al. |
| 7,439,358 B2 | 10/2008 | Linz et al. |
| 7,547,780 B2 | 6/2009 | Grauert et al. |
| 7,625,899 B2 | 12/2009 | Hoffmann et al. |
| 7,626,019 B2 | 12/2009 | Duran et al. |
| 7,629,460 B2 | 12/2009 | Grauert et al. |
| 2002/0183292 A1 | 12/2002 | Pairet et al. |
| 2002/0183293 A1 | 12/2002 | Banerjee et al. |
| 2003/0130286 A1 | 7/2003 | Denny et al. |
| 2004/0029885 A1 | 2/2004 | Bauer et al. |
| 2004/0147524 A1 | 7/2004 | Bauer et al. |
| 2004/0176380 A1 | 9/2004 | Hoffmann et al. |
| 2005/0014760 A1 | 1/2005 | Hoffmann et al. |
| 2005/0014761 A1 | 1/2005 | Hoffmann et al. |
| 2005/0148501 A1 | 7/2005 | Palmer et al. |
| 2005/0159414 A1 | 7/2005 | Nickolaus et al. |
| 2005/0165010 A1 | 7/2005 | Nickolaus et al. |
| 2006/0004014 A1 | 1/2006 | Hoffmann et al. |
| 2006/0009457 A1 | 1/2006 | Hoffmann et al. |
| 2006/0025411 A1 | 2/2006 | Hoffmann et al. |
| 2006/0035902 A1 | 2/2006 | Linz et al. |
| 2006/0035903 A1 | 2/2006 | Mohr et al. |
| 2006/0046989 A1 | 3/2006 | Grauert et al. |
| 2006/0047118 A1 | 3/2006 | Stadtmueller et al. |
| 2006/0052383 A1 | 3/2006 | Grauert et al. |
| 2006/0058311 A1 | 3/2006 | Munzert et al. |
| 2006/0074088 A1 | 4/2006 | Munzert et al. |
| 2006/0079503 A1 | 4/2006 | Schwede et al. |
| 2007/0208027 A1 | 9/2007 | Duran et al. |
| 2007/0213528 A1 | 9/2007 | Duran et al. |

(Continued)

FOREIGN PATENT DOCUMENTS

CA 2458699 A1 3/2003

(Continued)

OTHER PUBLICATIONS

Voskoglou-Nomikos, T. et al., "Clinical predictive value of the in vitro cell line, human xenograft, and mouse allograft preclinical cancer models". Clinical Cancer Research vol. 9, 2003, pp. 4227-4239.

(Continued)

*Primary Examiner*—James O Wilson
*Assistant Examiner*—Cecilia M Jaisle
(74) *Attorney, Agent, or Firm*—Michael P. Morris; Mary-Ellen M. Devlin; Anthony P. Bottino

(57) ABSTRACT

Disclosed are new dihydropteridinones of the formula (I)

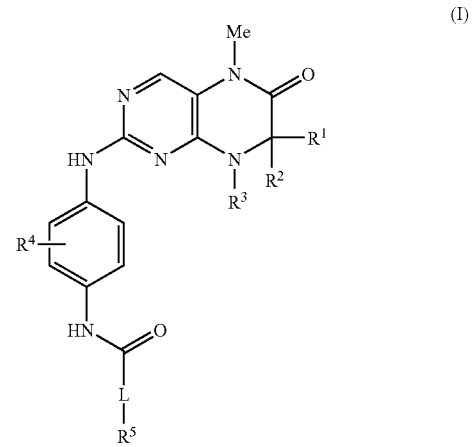

wherein the groups L, $R^1$, $R^2$, $R^3$, $R^4$ and $R^5$ have the meanings provided herein, the isomers thereof, processes for preparing these dihydropteridinones and their use as pharmaceutical compositions.

1 Claim, No Drawings

U.S. PATENT DOCUMENTS

| | | |
|---|---|---|
| 2007/0213529 A1 | 9/2007 | Duran et al. |
| 2007/0213530 A1 | 9/2007 | Duran et al. |
| 2007/0213531 A1 | 9/2007 | Duran et al. |
| 2007/0213534 A1 | 9/2007 | Duran et al. |
| 2007/0219369 A1 | 9/2007 | Duran et al. |
| 2008/0108812 A1 | 5/2008 | Grauert et al. |
| 2008/0113992 A1 | 5/2008 | Grauert et al. |
| 2008/0171747 A1 | 7/2008 | Hoffman et al. |
| 2008/0177066 A1 | 7/2008 | Linz et al. |
| 2008/0194818 A1 | 8/2008 | Grauert et al. |
| 2008/0221099 A1 | 9/2008 | Munzert et al. |
| 2008/0293944 A1 | 11/2008 | Hoffmann et al. |
| 2008/0319190 A1 | 12/2008 | Grauert et al. |
| 2008/0319192 A1 | 12/2008 | Grauert et al. |
| 2008/0319193 A1 | 12/2008 | Grauert et al. |
| 2009/0018333 A1 | 1/2009 | Grauert et al. |
| 2009/0030004 A1 | 1/2009 | Linz et al. |
| 2009/0124628 A1 | 5/2009 | Hoffmann et al. |
| 2009/0143379 A1 | 6/2009 | Mohr et al. |
| 2009/0238828 A1 | 9/2009 | Munzert et al. |
| 2009/0280115 A1 | 11/2009 | Maier et al. |
| 2009/0298840 A1 | 12/2009 | Linz et al. |

FOREIGN PATENT DOCUMENTS

| | | |
|---|---|---|
| CA | 2517020 A1 | 10/2004 |
| CA | 2517010 A1 | 11/2004 |
| CA | 2576290 A1 | 2/2006 |
| EP | 143478 A1 | 6/1985 |
| EP | 347146 A2 | 12/1989 |
| EP | 0399856 A1 | 11/1990 |
| EP | 0429149 A1 | 5/1991 |
| ES | 2287583 | 12/2007 |
| WO | 9609045 A1 | 3/1996 |
| WO | 9634867 A1 | 11/1996 |
| WO | 9636597 A1 | 11/1996 |
| WO | 9811893 A1 | 3/1998 |
| WO | 01/19825 A1 | 3/2001 |
| WO | 0170741 A1 | 9/2001 |
| WO | 0178732 A1 | 10/2001 |
| WO | 02057261 A2 | 7/2002 |
| WO | 02076954 A1 | 10/2002 |
| WO | 02076985 A | 10/2002 |
| WO | 03/020722 A1 | 3/2003 |
| WO | 03093249 A1 | 11/2003 |
| WO | 2004014899 A1 | 2/2004 |
| WO | 2004076454 A1 | 9/2004 |
| WO | 2004093848 A2 | 11/2004 |
| WO | 2005067935 A1 | 7/2005 |
| WO | 2006/018182 A1 | 2/2006 |
| WO | 2006/018221 A1 | 2/2006 |
| WO | 2006018185 A2 | 2/2006 |
| WO | 2006018220 A2 | 2/2006 |
| WO | 2006018221 A1 | 2/2006 |
| WO | 2006/021378 A1 | 3/2006 |
| WO | 2007090844 A1 | 8/2007 |
| WO | 2009019205 A1 | 2/2009 |

OTHER PUBLICATIONS

Wagner, B. et al, "7-Benzylamino-6-chloro-2-piperazino-4-pyrrolidino-pteridine, a potent inhibitor of cAMP-specific phosphodiesterase, enhancing nuclear protein binding to the CRE consensus sequence in human tumour cells", Biochemical Pharmacology, Pergamon, Oxford, GB, 2002, pp. 659-668.

Wagner, G. et al., "Synthesis of new phrido[3',2':4,5] thieno '3,2-d] 1,2,3-triazine derivatives as antianaphylactics". Biosciences Dept of the University of Leipzig, Pharmazie (Pharmacy), 48, vol. 7,1993, pp. 514-518.

Webster's Comprehensive Dictionary, 1996, pp. 1013-1014.

Wikipedia. "Melting Point", Jan. 17, 2007. http://en.wikipedia.org/wiki/Melting_point.

Masuda, et al., Oncogene (2003) 22, 1012-1023.

Ito, et al., "Polo-like kinase 1 (PLK1) expression is associated with cell proliferative activity and cdc2 expression in malignant lymphoma of the thyroid" Anticancer Research, 2004, vol. 24, No. 1, pp. 259-263 (hhttp://cat.inist.fr/?aModele=afficheN&cpsidt=15622521 Nov. 17, 2006—Abstract).

Mito, et al., "Expression of Polo-Like Kinase (PLK1) in non-Hodgkin's lymphomas," Leuk. Lymphoma, Feb. 2005, 46(2): 225-31 (PubMed abstract).

Verschuren, et al., "The cell cycle and how it is steered by Kaposi's sarcoma-associated herpesvirus cyclin" J. Gen. Virology (2004), 85, pp. 1347-1361.

Tor Ahlenius, Listing of cardiovascular disorders/diseases, Karolinska Instiutet Library, Stockholm, Sweden, http://www.mic.ki.se/diseases/c14.html, pp. 1-34, Apr. 2007.

Wolf, Donald E., et al., "The Structure of Rhizopterin", J. Am. Chem. Soc., vol. 69, pp. 2753-2759, 1947.

Ferrand, G. et al: "Synthesis and potential antiallergic activity of new pteridinones and related compounds." European Journal of Medicinal Chemistry, Vo. 31, #4, 1996, pp. 273-280.

Kimball, S.D., et al; Ann. Reports Med. Chem., vol. 36,2001, pp. 139-148.

Savelli, F.& Boido, A;. "Heterocyclic System Part II-Synthesis of New Pyrido [1'2':4,5] pyrazino [3,2-d] pyrimidines"; Bollettino Chimico Farmaceutico, 131(8), 309-12, Sep. 1992.

Katherine Arnold, "Collaboration to Play Key Role in NCI's Future, Director Says" Journal of the National Cancer Institute, Jun. 5, 2002, pp. 790-792, vol. 94, No. 11. Http://jncicancerspectrum.oxfordjournals.org/cgi/content/full/jnci;94/11/790.

The Merck Manual of Medical Information—Home Edition, Section 17, Parasitic Infections, Chapter 184 on the web site http://www.merck.com/mrkshared/mmanual_home/sec17/184.jsp, downloaded on Nov. 26, 2003.

Takai, et al., Oncongene, 2005, 24, pp. 287-291.

Karolinska Institutet, listing of cardiovascular disorders/diseases.

US Office Action mailed Dec. 10, 2003, U.S. Appl. No. 10/226,710.

US Office Action mailed Apr. 28, 2004, U.S. Appl. No. 10/374,876.

ACPS Meeting, Background Information. "Scientific considerations of plymorphism in pharmaceutical solids: abbreviated new drug applications". Oct. 2002.

Ahmad, N. "Polo-like kinase (PLK) 1: a novel target for the treatment of prostate cancer". The FASEB Journal. 2004, 18:5-7. Dept of Dermatology, Univ. Wisconsin, pp. 5-7.

BBC News/Health, Killer Breast Cancern Therapy Hope, www.newsvote.bbc/co./uk, downloaded Mar. 26, 2009.

Bennett, J.C., et al., "Textbook of Medicine", Part XIV, Oncology, 1997.

Blain, S. W. et al., "Differential interaction of the cyclin-dependent kinase (Cdk) Inhibitor p27KIP with cyclin A-Cdk2 and cyclin D2-Cdk4". The Journal of Biological Chemistry, vol. 272, No. 41, Issue Oct. 10, 1997, pp. 25862-25872.

Chen, J.X. et al., "Parallel differentiated recognition of ketones and acetals". Angewandte Chemie Int. Ed, vol. 37, Issue 1/2, p. 91-93, 1998.

Dipolar aprotic solvent. Exhibit A, IUPAC Compendium of Chemical Terminology, 2nd Edition, 1997.

Doerwald, F.Z. Book Wiley-VCH Verlag GmbH & Co. KGaA, "Side reactions in organice synthesis: A Guide to Successful Synthesis Design". 2005.

Eurasian Opinion, Appln No. 2007/00389/28, Maly Slatoustinsky per., d.10, kv.15, 101000 Moscow, Russia, "EVROMARKPAT", 2007.

Ghandi, L., et al., "An Open-Label Phase II Trial of the PLK Inhibitor BI 2536 in Patients with Sensitive Relapse Small Cell Lung Cancer". ASCO Meeting 2009.

Giron, G. "Thernal analysis and calorimetric methods in the characterization of plymorphs and solvates". Thermochimica Acta 248, 1995, pp. 1-59.

Goodman-Gilman's "The Pharmacological Basis of Therapeutics". Ninth edition, 1996, pp. 1225-1271.

International Seach Report for PCT/EP2007/051139 mailed May 29, 2007.

International Search Report for PCT/EP03/01935 mailed Jul. 23, 2003.
International Search Report for PCT/EP2005/006404 mailed Nov. 14, 2005.
International Search Report for PCT/EP2005/007532 mailed Oct. 6, 2005.
International Search Report for PCT/EP2005/008736 mailed Nov. 30, 2005.
International Search Report for PCT/EP2005/008990 mailed Dec. 13, 2005.
International Search Report for PCT/EP2005/054096 mailed Jan. 24, 2006.
Jamieson, C. et al., "Application of ReactArray Robotics and Design of Experiments Techniques in Optimisation of Supported Reagent Chemistry". Org. Proc. Res. & Dev., 2002, 6, p. 823-825.
Jaworska, J., et al., "Review of methods for assessing the applicability domains of SARS and QSARS". Sponsor: The European Commission—Joint Research Ctr., Institute for Health and Consumer Protection—ECVAM, Italy, 2004.
Kashima, M. K. et al., "Expression of polo-like kinase (PLK1) in non-Hodgkin's lymphomas". NCBI, PubMed, 2005.
Leukemia & Lymphoma Society—Disease Information-Lymphoma. www.leukemia-lymphoma.org/all_page?item_id-7030, downloaded Mar. 26, 2009.
Leukemia & Lymphoma Society—Disease Information. www.leukemia-lymphoma.org/all_page?item_id-7026, downloaded Mar. 26, 2009.
Marko, D. et al., "Intracellular localization of 7-benzylamino-6-chloro-2-piperazino-4-pyrrolidino-pteridine in membrane structures impeding the inhibition of cytosolic cyclic AMP-specific phosphodiesterase". Biochemical Pharmacology, 63, 2002, pp. 669-676.
Mayer, SF, et al., "Enzyme-initiated domino (cascase) reactions". Chem. Soc. Rev, 2001, p. 332-339.
MedlinePlus: Bacterial Infections. www.nim.nih.gov/medlineplus/print/bacterialinfections.htm, downloaded Mar. 26, 2009.
MedlinePlus: Viral Infections. www.nim.nih.gov/medlineplus/print/viralinfections.htm, downloaded Mar. 26, 2009.
Nagao, K. et al., "Effect of MX-68 on airway inflammation and hyperresponsiveness in mice and guinea-pigs". Journal of Pharmacy and Pharmacology, JPP 2004, 56, pp. 187-196.
National Institute of Neurological Disorders, Index Stroke, 2006.
National Kidney Foundation: Chronic Kidney Disease (CKD). www.kidney.org/kidneydisease/ckd/index.cfm, downloaded Mar. 26, 2009.
Norman, P. "PDE4 inhibitors". Ashley Publications Ltd., Expert Opinions Ther. Patents, 1999, pp. 1101-1118.
Ohio Dept of Health, "Brain and Other Central Nervous System Cancer in Ohio, 1997-2001". Sep. 2004, pp. 1-4.
Organic Chemistry, Grupo Editorial Iberoamerica, Section 13, 3, pp. 301-302, 1983 (best copy available in Spanish).
Rylander, P.N. "Hydrgenation Methods". 1985, Chapter 13.
Rylander, P.N. "Hydrgenation Methods". 1985, Chapters 3, 4.
Rylander, P.N. "Hydrgenation Methods". 1985, Chapters 8, 9, 10, 11.
Rylander, P.N. "Hydrgenation Methods". 1985, Chapter 5, 6, 7.
Rylander, P.N., "Hydrogenation Methods". 1985, Chapters 1, 2.
Santing, R. E. et al., "Brochodilatory and anti-inflammatory properties of inhaled selective phosphodiesterase inhibitors in a guinea pig model of allergic asthma". European Journal of Pharmacology, 429, 2001, pp. 335-344.
Science, vol. 310, Oct. 21, 2005, p. 409, Chemistry: One After Another.
Snyder, J. S. et al., "Common bacteria whose susceptibility to antimicrobials is no longer predictable". NCBI, PubMed, 2000, Le Journal Medical Libanais (The Lebanse Medical Journal), 48, pp. 208-214.
Souillac, P. et al., "Characterization of delivery systems, differential scanning calorimetry". (In Encyclopedia of Controlled Drug Delivery), 1999, John Wiley & Sons, pp. 212-227.
Sugar, A. M. et al., "Comparison of three methods of antifungal susceptibility testing with the proposed NCCLS standard broth macrodilution assay: lack of effect of phenol red". Mycology, Diagn Microbiol. Infect. Dis. 1995, 21- pp. 129-133.
Tenbrink, R. E. et al., "Antagonist, partial agonist, and full agonist imidazo[1,5-a]quinoxaline amides and carbamates acting through the BABA/Benzodiazepine receptor". J. Med. Chem. 1994, 37, pp. 758-768.
Turner, S., "The Design of Organic Syntheses". Elsevier, 1976, pp. 10 and 149.
Turner, W.W.et al., "Recent advances in the medicinal chemistry of antifungal agents". Current Pharmacutical Design, 1996, 2, pp. 209-224.
Vippagunta, S. R. et al., "Crystalline solids". Advanced Drug Delivery Reviews, 48, 2001, pp. 3-26.
Viral Defense Foundation. www.viraldefense.org/mission.htm, downloaded Mar. 26, 2009.
Visiting Nurse Association of America. www.vnaa.org/gen/Germ_Protection_Center_Cold_and_Flu_Resources,html, downloaded Mar. 26, 2009.

DIHYDROPTERIDIONE DERIVATIVES, PROCESS FOR THEIR MANUFACTURE AND THEIR USE AS MEDICAMENT

APPLICATION DATA

This application is a divisional application of U.S. application Ser. No. 11/210,379 filed on Aug. 24, 2005 which claims benefit to European Patent Application no. EP 04 020 124.6 filed Aug. 25, 2004.

FIELD OF INVENTION

The present invention relates to new dihydropteridinones of general formula (I)

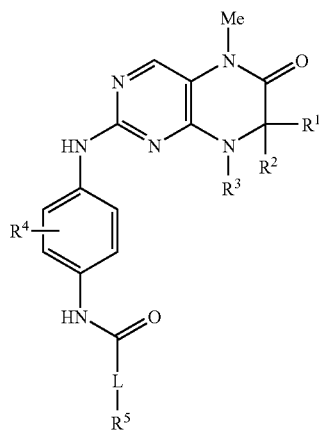

(I)

wherein the groups L, $R^1$, $R^2$, $R^3$, $R^4$ and $R^5$ have the meanings given in the claims and specification, the isomers thereof, processes for preparing these dihydropteridinones and their use as pharmaceutical compositions.

BACKGROUND TO THE INVENTION

Pteridinone derivatives are known from the prior art as active substances with an antiproliferative activity. WO 01/019825 and WO 03/020722 describe the use of pteridinone derivatives for the treatment of tumoral diseases.

Tumour cells wholly or partly elude regulation and control by the body and are characterised by uncontrolled growth. This is based on the one hand on the loss of control proteins, such as e.g. Rb, p16, p21 and p53 and also on the activation of so-called accelerators of the cell cycle, the cyclin-dependent kinases (CDK's).

In addition, the protein kinase Aurora B has been described as having an essential function during entry into mitosis. Aurora B phosphorylates histone H3 at Ser10 and thus initiates chromosome condensation (Hsu et al. 2000, *Cell* 102: 279-91). A specific cell cycle arrest in the G2/M phase may however also be triggered e.g. by the inhibition of specific phosphatases such as e.g. Cdc25C (Russell and Nurse 1986, *Cell* 45:145-53). Yeasts with a defective Cdc25 gene arrest in the G2 phase, while overexpression of Cdc25 leads to premature entry into the mitosis phase (Russell and Nurse 1987, *Cell* 49:559-67). Moreover, an arrest in the G2/M phase may also be triggered by the inhibition of certain motor proteins, the so-called kinesins such as e.g. Eg5 (Mayer et al. 1999, *Science* 286:971-4), or by agents which stabilise or destabilise microtubules (e.g. colchicin, taxol, etoposide, vinblastin, vincristine) (Schiff and Horwitz 1980, *Proc Natl Acad Sci USA* 77:1561-5).

In addition to the cyclin-dependent and Aurora kinases the so-called polo-like kinases, a small family of serine/threonine kinases, play an important part in the regulation of the eukaryotic cell cycle. Hitherto, the polo-like kinases PLK-1, PLK-2, PLK-3 and PLK-4 have been described in the literature. PLK-1 in particular has been shown to play a central part in the regulation of the mitosis phase. PLK-1 is responsible for the maturation of the centrosomes, for the activation of phosphatase Cdc25C, and for the activation of the Anaphase Promoting Complex (Glover et al. 1998, *Genes Dev.* 12:3777-87; Qian et al. 2001, *Mol Biol Cell.* 12:1791-9). The injection of PLK-1 antibodies leads to a G2 arrest in untransformed cells, whereas tumour cells arrest in the mitosis phase (Lane and Nigg 1996, *J Cell Biol.* 135:1701-13). Overexpression of PLK-1 has been demonstrated for various types of tumour, such as non-small-cell lung cancer, plate epithelial carcinoma, breast and colorectal carcinoma (Wolf et al. 1997, *Oncogene* 14:543-549; Knecht et al. 1999, *Cancer Res.* 59:2794-2797; Wolf et al. 2000, *Pathol. Res. Pract.* 196:753-759; Takahashi et al. 2003, *Cancer Sci.* 94:148-52). Therefore, this category of proteins also constitutes an interesting approach to therapeutic intervention in proliferative diseases (Liu and Erikson 2003, *Proc Natl Acad Sci USA* 100:5789-5794).

The resistance of many types of tumours calls for the development of new pharmaceutical compositions for combating tumours.

The aim of the present invention is to provide new compounds having an antiproliferative activity.

DESCRIPTION OF THE INVENTION

The problem according to the invention is solved by the following compounds of formula (I).

Accordingly, the present invention relates to dihydropteridinones of general formula (I)

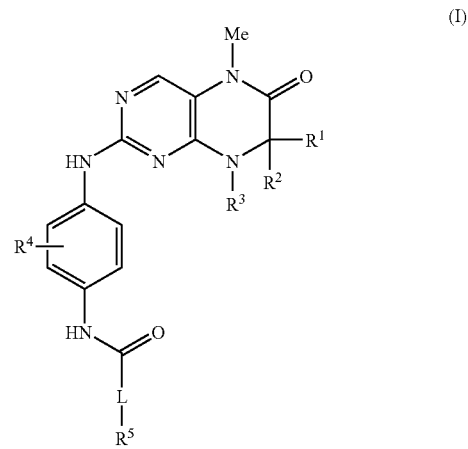

(I)

wherein

L denotes a single bond, or a bridging double-bonded group selected from among $C_1$-$C_6$-alkylene, $C_2$-$C_6$-alkenylene, $C_2$-$C_6$-alkynylene, $C_3$-$C_7$-cycloalkylene, $C_1$-$C_4$-alkylene-$C_6$-$C_{10}$-arylene-$C_1$-$C_4$-alkylene, $C_1$-$C_4$-alkylene-$C_6$-$C_{10}$-arylene, —O—, —O—$C_1$-$C_6$-alkylene, —O—$C_3$-$C_6$-alkenylene, —O—$C_3$-$C_6$-alkynylene, —O—$C_3$-$C_7$- cycloalkylene, —O—$C_1$-$C_4$-alkylene-$C_6$-$C_{10}$-arylene-$C_1$-$C_4$-alkylene, —O—$C_1$-$C_4$-alkylene-$C_6$-$C_{10}$-arylene, —$NR^7$— and —$NR^7$—$C_1$-$C_6$-alkylene, —$NR^7$—$C_3$-$C_6$-alkenylene, —$NR^7$—$C_3$-$C_6$-alkynylene, —$NR^7$—$C_3$-$C_7$-cycloalkylene, —$NR^7$—$C_1$-$C_4$-alkylene-$C_6$-$C_{10}$-arylene-$C_1$-$C_4$-alkylene, —$NR^7$—$C_1$-$C_4$-alkylene-$C_6$-$C_{10}$-arylene, which may optionally be substituted by one or more groups $R^9$;

$R^1$ and $R^2$, which may be identical or different, denote hydrogen, or a group selected from among $C_1$-$C_6$-alkyl, $C_2$-$C_6$-alkenyl and $C_2$-$C_6$-alkynyl, which may optionally be mono- or polysubstituted by one or more groups $R^9$, or $R^1$ and $R^2$ together denote $C_2$-$C_6$-alkylene, in which optionally one or two methylene groups may be replaced by one of the groups —O or —$NR^7$, and which may optionally be mono- or polysubstituted by one or more groups $R^9$;

$R^3$ denotes hydrogen or a group selected from $C_1$-$C_8$-alkyl, $C_2$-$C_8$-alkenyl, $C_2$-$C_8$-alkynyl, $C_3$-$C_8$-cycloalkyl and $C_6$-$C_{14}$-aryl, which may optionally be mono- or polysubstituted by one or more groups $R^9$; or $R^1$ and $R^2$ or $R^3$ and $R^1$ together denote $C_2$-$C_6$-alkylene which may optionally be mono- or polysubstituted by one or more groups $R^9$;

$R^4$ denotes hydrogen, halogen, CN, OH, —$NR^7R^8$ or a group selected from among $C_1$-$C_6$-alkyl, $C_1$-$C_6$-alkyloxy, $C_2$-$C_6$-alkenyl, $C_2$-$C_6$-alkenyloxy, $C_2$-$C_6$-alkynyl and $C_2$-$C_6$-alkynyloxy, which may optionally be mono- or polysubstituted by one or more groups $R^{10}$;

$R^5$ denotes $C_3$-$C_8$-cycloalkyl which may optionally be mono- or polysubstituted by one or more groups $R^6$, or $R^5$ denotes $C_3$-$C_8$-cycloalkyl which may optionally be mono- or polysubstituted by one or more groups $R^9$, or $R^5$ denotes a 5-10-membered heteroaryl group which may contain one, two or three heteroatoms selected from among nitrogen, oxygen and sulphur, preferably nitrogen or oxygen, and which may optionally be mono- or polysubstituted by one or more of the groups $R^{11}$, or $R^5$ denotes a 5-10-membered heterocycloalkyl group which may contain one, two or three heteroatoms selected from among nitrogen, oxygen and sulphur, preferably nitrogen or oxygen, and which may optionally be mono- or polysubstituted by one or more of the groups $R^{11}$;

$R^6$ denotes —$NR^7R^8$ or a 5-10-membered heterocycloalkyl group which may contain one, two or three heteroatoms selected from among nitrogen, oxygen and sulphur, preferably nitrogen or oxygen, and which may optionally be mono- or polysubstituted by one or more of the groups $R^{12}$;

$R^7$ and $R^8$, which may be identical or different, denote hydrogen or $C_1$-$C_6$-alkyl, $R^9$ denotes halogen, CN, OH or $CF_3$;

$R^{10}$ denotes halogen, OH, CN, =O, $C_1$-$C_6$-alkyloxy, $COOR^7$, $NR^7R^8$, $CONR^7R^8$, $SO_2R^7$, $CHF_2$ or $CF_3$;

$R^{11}$ denotes halogen, $C_1$-$C_4$-alkyl, OH, $CF_3$, $C_6$-$C_{10}$-aryl or $C_1$-$C_6$-alkylene-$C_6$-$C_{10}$-aryl;

$R^{12}$ denotes halogen, $CF_3$, $C_1$-$C_6$-alkyl, $C_3$-$C_8$-cycloalkyl or $C_1$-$C_6$-alkylene-$C_3$-$C_8$-cycloalkyl;

optionally in the form of the tautomers, racemates, enantiomers, diastereomers and mixtures thereof, and optionally in the form of the pharmacologically acceptable acid addition salts, solvates and/or hydrates thereof.

Preferred are compounds of general formula (I), wherein

L denotes a single bond, or a bridging double-bonded group selected from among $C_1$-$C_6$-alkylene, $C_2$-$C_6$-alkenylene, $C_2$-$C_6$-alkynylene, $C_3$-$C_7$-cycloalkylene, $C_1$-$C_4$-alkylene-$C_6$-$C_{10}$-arylene-$C_1$-$C_4$-alkylene, —O, —O—$C_1$-$C_4$-alkylene, —$NR^7$— and —$NR^7$—$C_1$-$C_4$-alkylene, which may optionally be substituted by one or more groups $R^9$;

$R^1$ and $R^2$, which may be identical or different, denote hydrogen, or a group selected from among $C_1$-$C_6$-alkyl, $C_2$-$C_6$-alkenyl and $C_2$-$C_6$-alkynyl, which may optionally be mono- or polysubstituted by one or more groups $R^9$, or $R^1$ and $R^2$ together denote $C_2$-$C_6$-alkylene, in which optionally one or two methylene groups may be replaced by one of the groups —O or —$NR^7$, and which may optionally be mono- or polysubstituted by one or more groups $R^9$;

$R^3$ denotes hydrogen or a group selected from $C_1$-$C_8$-alkyl, $C_2$-$C_8$-alkenyl, $C_2$-$C_8$-alkynyl, $C_3$-$C_8$-cycloalkyl and $C_6$-$C_{14}$-aryl, which may optionally be mono- or polysubstituted by one or more groups $R^9$; or $R^3$ and $R^2$ or $R^3$ and $R^1$ together denote $C_2$-$C_6$-alkylene which may optionally be mono- or polysubstituted by one or more groups $R^9$;

$R^4$ denotes hydrogen, halogen, CN, OH, —$NR^7R^8$ or a group selected from among $C_1$-$C_6$-alkyl, $C_1$-$C_6$-alkyloxy, $C_2$-$C_6$-alkenyl, $C_2$-$C_6$-alkenyloxy, $C_2$-$C_6$-alkynyl and $C_2$-$C_6$-alkynyloxy, which may optionally be mono- or polysubstituted by one or more groups $R^{10}$;

$R^5$ denotes $C_3$-$C_8$-cycloalkyl, which may optionally be substituted by a group $R^6$, or $R^5$ denotes $C_3$-$C_8$-cycloalkyl which may optionally be mono- or polysubstituted by one or more groups $R^9$, or $R^5$ denotes a 5-10-membered heteroaryl group which may contain one, two or three heteroatoms selected from among nitrogen, oxygen and sulphur, preferably nitrogen or oxygen, and which may optionally be mono- or polysubstituted by one or more of the groups $R^9$, or $R^5$ denotes a 5-10-membered heterocycloalkyl group which may contain one, two or three heteroatoms selected from among nitrogen, oxygen and sulphur, preferably nitrogen or oxygen, and which may optionally be mono- or polysubstituted by one or more of the groups $R^{11}$;

$R^6$ denotes —$NR^7R^8$ or a 5-10-membered heterocycloalkyl group which may contain one, two or three heteroatoms selected from among nitrogen, oxygen and sulphur, preferably nitrogen or oxygen, and which may optionally be mono- or polysubstituted by one or more of the groups $R^{12}$;

$R^7$ and $R^8$, which may be identical or different, denote hydrogen or $C_1$-$C_6$-alkyl, $R^9$ denotes halogen, CN, OH or $CF_3$;

$R^{10}$ denotes halogen, OH, CN, =O, $C_1$-$C_6$-alkyloxy, $COOR^7$, $CONR^7R^8$, $SO_2R^7$, $CHF_2$ or $CF_3$;

$R^{11}$ denotes halogen, $C_1$-$C_4$-alkyl, OH, $CF_3$, $C_6$-$C_{10}$-aryl or $C_1$-$C_6$-alkylene-$C_6$-$C_{10}$-aryl;

$R^{12}$ denotes halogen, $CF_3$, $C_1$-$C_6$-alkyl, $C_3$-$C_8$-cycloalkyl or $C_1$-$C_6$-alkylene-$C_3$-$C_8$-cycloalkyl;

optionally in the form of the tautomers, racemates, enantiomers, diastereomers and mixtures thereof, and optionally in the form of the pharmacologically acceptable acid addition salts, solvates and/or hydrates thereof.

Also preferred are compounds of general formula (I), wherein

L denotes a single bond, —O, —O—$C_1$-$C_3$-alkylene, —$NR^7$, —$NR^7$—$C_1$-$C_3$-alkylene or $C_1$-$C_4$-alkylene, which may optionally be substituted by one or more groups $R^9$;

$R^1$ and $R^2$, which may be identical or different, denote hydrogen, or a group selected from among $C_1$-$C_4$-alkyl, $C_2$-$C_4$-alkenyl and $C_2$-$C_4$-alkynyl, which may optionally be mono- or polysubstituted by one or more groups $R^9$, or $R^1$ and $R^2$ together denote $C_2$-$C_4$-alkylene which may optionally be mono- or polysubstituted by one or more groups $R^9$;

$R^3$ denotes hydrogen or a group selected from $C_1$-$C_6$-alkyl, $C_3$-$C_7$-cycloalkyl and $C_6$-$C_{10}$-aryl, which may optionally be mono- or polysubstituted by one or more groups $R^9$; or $R^3$ and $R^2$ or $R^3$ and $R^1$ together denote $C_2$-$C_4$-alkylene which may optionally be mono- or polysubstituted by one or more groups $R^9$;

$R^4$ denotes hydrogen, fluorine, chlorine, bromine, —$NR^7R^8$ or a group selected from among $C_1$-$C_4$-alkyl, $C_1$-$C_4$-alkyloxy, $C_2$-$C_4$-alkenyloxy and $C_2$-$C_4$-alkynyloxy, which may optionally be mono- or polysubstituted by one or more groups $R^{10}$;

$R^5$ denotes $C_3$-$C_7$-cycloalkyl, which may optionally be substituted by a group $R^6$, or $R^5$ denotes $C_3$-$C_7$-cycloalkyl which may optionally be mono- or polysubstituted by one or more groups $R^9$, or $R^5$ denotes a heteroaryl selected from among imidazolyl, oxazolyl, isoxazolyl, pyrolyl, pyrazolyl, oxadiazolyl, pyridyl, pyridazinyl, pyrazinyl, pyrimidinyl, indolyl, quinolinyl, isoquinolinyl, benzimidazolyl, purinyl and pteridinyl, which may optionally be mono- or polysubstituted by one or more of the groups $R^{11}$, or $R^5$ denotes a heterocycloalkyl selected from among piperidinyl, piperazinyl, pyrrolinyl, pyrrolidinyl, pyrazolinyl, pyrazolidinyl, imidazolinyl, imidazolidinyl and morpholinyl which may optionally be mono- or polysubstituted by one or more of the groups $R^{11}$;

$R^6$ denotes a heterocycloalkyl selected from among piperidinyl, piperazinyl, pyrrolinyl, pyrrolidinyl, pyrazolinyl, pyrazolidinyl, imidazolinyl, imidazolidinyl and morpholinyl which may optionally be mono- or polysubstituted by one or more of the groups $R^{12}$;

$R^7$ and $R^8$, which may be identical or different, denote hydrogen or $C_1$-$C_4$-alkyl, $R^9$ denotes halogen, OH, =O or $CF_3$;

$R^{10}$ denotes halogen, OH, =O, $C_1$-$C_4$-alkyloxy or $CF_3$;

$R^{11}$ denotes halogen, $C_1$-$C_4$-alkyl, OH, $CF_3$, phenyl or $C_1$-$C_4$-alkylene-phenyl;

$R^{12}$ denotes $C_1$-$C_4$-alkyl, $C_3$-$C_6$-cycloalkyl or $C_1$-$C_4$-alkylene-$C_3$-$C_6$-cycloalkyl;

optionally in the form of the tautomers, racemates, enantiomers, diastereomers and mixtures thereof, and optionally in the form of the pharmacologically acceptable acid addition salts, solvates and/or hydrates thereof.

Also preferred are compounds of general formula (I), wherein

L denotes a single bond, $C_1$-$C_4$-alkylene, —O or NH—;

$R^1$ and $R^2$, which may be identical or different, denote hydrogen, or a group selected from among $C_1$-$C_4$-alkyl, $C_2$-$C_4$-alkenyl and $C_2$-$C_4$-alkynyl, which may optionally be mono- or disubstituted by a group selected from among fluorine, chlorine, OH and $CF_3$; or $R^3$ denotes hydrogen or a group selected from $C_1$-$C_6$-alkyl, $C_3$-$C_7$-cycloalkyl and $C_6$-$C_{10}$-aryl, which may optionally be mono- or disubstituted by a group selected from among fluorine, chlorine, OH and $CF_3$; or $R^4$ denotes hydrogen, fluorine, chlorine, bromine, —$NR^7R^8$ or a group selected from among $C_1$-$C_4$-alkyl, $C_1$-$C_4$-alkyloxy, $C_2$-$C_4$-alkenyloxy and $C_2$-$C_4$-alkynyloxy, which may optionally be mono- or disubstituted by a group selected from among fluorine, chlorine, OH, methoxy, ethoxy and $CF_3$;

$R^5$ denotes $C_3$-$C_7$-cycloalkyl, which may optionally be mono- or disubstituted by a group selected from among methyl, ethyl, propyl OH, fluorine, chlorine, $CF_3$ and $R^6$, or $R^5$ denotes a heteroaryl selected from among imidazolyl, oxazolyl, isoxazolyl, pyrolyl, pyrazolyl, oxadiazol, pyridyl, pyridazinyl, pyrazinyl, pyrimidinyl, indolyl, quinolinyl, isoquinolinyl, benzimidazolyl, purinyl and pteridinyl, which may optionally be mono- or disubstituted, preferably monosubstituted, by fluorine, chlorine, OH, $CF_3$, methyl, ethyl, propyl, phenyl, benzyl or phenethyl;

$R^5$ denotes a heterocycloalkyl selected from among piperidinyl, piperazinyl, pyrrolinyl, pyrrolidinyl, pyrazolinyl, pyrazolidinyl, imidazolinyl, imidazolidinyl and morpholinyl, which may optionally be mono- or disubstituted, preferably monosubstituted, by fluorine, chlorine, OH, $CF_3$, methyl, ethyl, propyl, phenyl, benzyl or phenethyl;

$R^6$ denotes a heterocycloalkyl selected from among piperidinyl, piperazinyl, pyrrolinyl, pyrrolidinyl, pyrazolinyl, pyrazolidinyl, imidazolinyl, imidazolidinyl and morpholinyl, which may be mono- or disubstituted by methyl, ethyl, cyclopropyl or cyclopropylmethyl;

$R^7$ and $R^8$, which may be identical or different, denote hydrogen or $C_1$-$C_4$-alkyl, optionally in the form of the tautomers, racemates, enantiomers, diastereomers and mixtures thereof, and optionally in the form of the pharmacologically acceptable acid addition salts, solvates and/or hydrates thereof.

Also preferred are compounds of general formula (I), wherein

L denotes a single bond, —$CH_2$, —$CH_2$—$CH_2$, —O or NH—;

$R^1$ and $R^2$, which may be identical or different, denote hydrogen or a group selected from among methyl, ethyl, propyl, butyl, allyl and propargyl, which may optionally be mono- or disubstituted by a group selected from among fluorine, chlorine and $CF_3$;

$R^3$ denotes hydrogen or a group selected from among methyl, ethyl, propyl, butyl, pentyl, cyclopropyl, cyclopentyl, cyclohexyl and phenyl, which may optionally be mono- or disubstituted by a group selected from among fluorine, chlorine and $CF_3$;

$R^4$ denotes hydrogen, methyl, ethyl, propyl, methyloxy, ethyloxy or propyloxy;

$R^5$ denotes $C_3$-$C_6$-cycloalkyl, which may optionally be mono- or disubstituted, preferably monosubstituted, by methyl, ethyl, propyl OH, fluorine, chlorine, $CF_3$ or $R^6$, or $R^5$ denotes a heteroaryl selected from among pyridyl, pyrollyl and pyrimidinyl, which may optionally be mono- or disubstituted, preferably monosubstituted, by fluorine, chlorine, OH, $CF_3$, methyl, ethyl, propyl, phenyl, benzyl or phenethyl, $R^5$ denotes a heterocycloalkyl selected from among piperidinyl, piperazinyl, pyrrolidinyl and morpholinyl, which may optionally be mono- or disubstituted, preferably monosubstituted, by fluorine, chlorine, OH, $CF_3$, methyl, ethyl, propyl, phenyl, benzyl or phenethyl, $R^6$ denotes a heterocycloalkyl selected from among piperidinyl, morpholinyl, pyrrolidinyl and piperazinyl, which may optionally be mono- or disubstituted by methyl, ethyl, cyclopropyl or cyclopropylmethyl, optionally in the form of the tautomers, racemates, enantiomers, diastereomers and mixtures thereof, and optionally in the form of the pharmacologically acceptable acid addition salts, solvates and/or hydrates thereof.

Of particular importance according to the invention are compounds of general formula (I), wherein L denotes a single bond, or a bridging double-bonded group selected from among $C_1$-$C_4$-alkylene, $C_2$-$C_4$-alkenylene, $C_2$-$C_4$-alkynylene, $C_3$-$C_6$-cycloalkylene, —O, —O—$C_1$-

$C_3$-alkylene, —$NR^7$— and —$NR^7$—$C_1$-$C_3$-alkylene, which may optionally be substituted by one or more groups $R^9$, and the groups $R^1$, $R^2$, $R^3$, $R^4$ and $R^5$ and $R^9$ may have one of the meanings given above or hereinafter, optionally in the form of the tautomers, racemates, enantiomers, diastereomers and mixtures thereof, and optionally in the form of the pharmacologically acceptable acid addition salts, solvates and/or hydrates thereof.

Also of particular importance according to the invention are compounds of general formula (I), wherein L denotes a single bond, —O, —NH or $C_1$-$C_4$-alkylene, preferably a single bond —NH, —$CH_2$ or —$CH_2$—$CH_2$—, particularly preferably a single bond or —NH— and the groups $R^1$, $R^2$, $R^3$, $R^4$ and $R^5$ may have one of the meanings given above or hereinafter, optionally in the form of the tautomers, racemates, enantiomers, diastereomers and mixtures thereof, and optionally in the form of the pharmacologically acceptable acid addition salts, solvates and/or hydrates thereof.

Of particular importance according to the invention are compounds of general formula (I), wherein $R^1$ denotes hydrogen, methyl, ethyl, allyl or propargyl, preferably hydrogen or methyl, particularly preferably hydrogen and the groups L, $R^2$, $R^3$, $R^4$ and $R^5$ may have one of the meanings given above or hereinafter, optionally in the form of the tautomers, racemates, enantiomers, diastereomers and mixtures thereof, and optionally in the form of the pharmacologically acceptable acid addition salts, solvates and/or hydrates thereof.

Of particular importance according to the invention are compounds of general formula (I), wherein $R^2$ denotes hydrogen, methyl, ethyl, allyl or propargyl, preferably methyl or ethyl, and the groups L, $R^1$, $R^3$, $R^4$ and $R^5$ may have one of the meanings given above or hereinafter, optionally in the form of the tautomers, racemates, enantiomers, diastereomers and mixtures thereof, and optionally in the form of the pharmacologically acceptable acid addition salts, solvates and/or hydrates thereof.

Of particular importance according to the invention are compounds of general formula (I), wherein $R^3$ denotes ethyl, propyl, butyl, pentyl, cyclopropyl, cyclopentyl, cyclohexyl or phenyl, preferably propyl, butyl, pentyl, cyclopentyl or cyclohexyl, particularly preferably propyl, butyl, pentyl, cyclopentyl or cyclohexyl, whereas propyl, pentyl, cyclopentyl or cyclohexyl, particularly cyclopentyl and cyclohexyl are of particular importance, and the groups L, $R^1$, $R^2$, $R^4$ and $R^5$ may have one of the meanings given above or hereinafter, optionally in the form of the tautomers, racemates, enantiomers, diastereomers and mixtures thereof, and optionally in the form of the pharmacologically acceptable acid addition salts, solvates and/or hydrates thereof.

Of particular importance according to the invention are compounds of general formula (I), wherein $R^4$ denotes hydrogen, methyl, ethyl, methyloxy or ethyloxy, preferably hydrogen, methyl or methyloxy, particularly preferably hydrogen or methyloxy, and the groups L, $R^1$, $R^2$, $R^3$ and $R^5$ may have one of the meanings given above or hereinafter, optionally in the form of the tautomers, racemates, enantiomers, diastereomers and mixtures thereof, and optionally in the form of the pharmacologically acceptable acid addition salts, solvates and/or hydrates thereof.

Of particular importance according to the invention are compounds of general formula (I), wherein $R^5$ denotes a group selected from among cyclopropyl, cyclopentyl or cyclohexyl, which may optionally be mono- or disubstituted, preferably monosubstituted, by methyl, ethyl, OH, fluorine, chlorine, $CF_3$, piperidinyl, morpholinyl, pyrrolidinyl or piperazinyl, while the above-mentioned possible substituents piperidinyl, morpholinyl, pyrrolidinyl and piperazinyl may in turn be mono- or disubstituted by methyl, ethyl, cyclopropyl or cyclopropylmethyl, and the groups L, $R^1$, $R^2$, $R^3$ and $R^4$ may have one of the meanings given above or hereinafter, optionally in the form of the tautomers, racemates, enantiomers, diastereomers and mixtures thereof, and optionally in the form of the pharmacologically acceptable acid addition salts, solvates and/or hydrates thereof.

Of particular importance according to the invention are compounds of general formula (I), wherein $R^5$ denotes a group selected from among cyclopentyl or cyclohexyl, which may optionally be mono- or disubstituted, preferably monosubstituted, by methyl, fluorine, $CF_3$, morpholinyl or piperazinyl, while the above-mentioned possible substituents morpholinyl and piperazinyl may in turn be mono- or disubstituted, preferably monosubstituted, by methyl, ethyl or cyclopropylmethyl, and the groups L, $R^1$, $R^2$, $R^3$ and $R^4$ may have one of the meanings given above or hereinafter, optionally in the form of the tautomers, racemates, enantiomers, diastereomers and mixtures thereof, and optionally in the form of the pharmacologically acceptable acid addition salts, solvates and/or hydrates thereof.

Of particular importance according to the invention are compounds of general formula (I), wherein $R^5$ denotes a heteroaryl selected from among imidazolyl, oxazolyl, isoxazolyl, pyrolyl, pyrazolyl, oxadiazolyl, pyridyl, pyridazinyl, pyrazinyl, pyrimidinyl, indolyl, quinolinyl, isoquinolinyl, benzimidazolyl, purinyl and pteridinyl, which may optionally be mono- or disubstituted, preferably monosubstituted, by fluorine, chlorine, OH, $CF_3$, methyl, ethyl, propyl, phenyl, benzyl or phenethyl, and the groups L, $R^1$, $R^2$, $R^3$ and $R^4$ may have one of the meanings given above or hereinafter, optionally in the form of the tautomers, racemates, enantiomers, diastereomers and mixtures thereof, and optionally in the form of the pharmacologically acceptable acid addition salts, solvates and/or hydrates thereof.

Of particular importance according to the invention are compounds of general formula (I), wherein $R^5$ denotes a heteroaryl selected from among imidazolyl, pyrolyl, pyridyl, pyrimidinyl, quinolinyl, isoquinolinyl and benzimidazolyl, preferably selected from pyridyl, pyrollyl and pyrimidinyl, which may optionally be monoor disubstituted, preferably monosubstituted, by fluorine, chlorine, $CF_3$, methyl, ethyl, phenyl or benzyl, and the groups L, $R^1$, $R^2$, $R^3$ and $R^4$ may have one of the meanings given above or hereinafter, optionally in the form of the tautomers, racemates, enantiomers, diastereomers and mixtures thereof, and optionally in the form of the pharmacologically acceptable acid addition salts, solvates and/or hydrates thereof.

Of particular importance according to the invention are compounds of general formula (I), wherein $R^5$ denotes a heteroaryl selected from among imidazolyl, pyrolyl, pyridyl, pyrimidinyl, quinolinyl, isoquinolinyl and benzimidazolyl, preferably selected from pyridyl, pyrolyl and pyrimidinyl, which may optionally be mono- or disubstituted, preferably monosubstituted, by fluorine, chlorine, $CF_3$, methyl, ethyl, phenyl or benzyl, and the groups L, $R^1$, $R^2$, $R^3$ and $R^4$ may have one of the meanings given above or hereinafter, optionally in the form of the tautomers, racemates, enantiomers, diastereomers and mixtures thereof, and optionally in the form of the pharmacologically acceptable acid addition salts, solvates and/or hydrates thereof.

The term alkyl groups, including alkyl groups which are a part of other groups, denotes branched and unbranched alkyl groups with 1 to 8 carbon atoms, preferably 1-6, most preferably 1-4 carbon atoms. Examples include: methyl, ethyl, propyl, butyl, pentyl, hexyl, heptyl and octyl. Unless otherwise stated, the abovementioned terms propyl, butyl, pentyl, hexyl, heptyl and octyl include all the possible isomeric forms. For example, the term propyl includes the two isomeric groups n-propyl and iso-propyl, the term butyl includes n-butyl, iso-butyl, sec. butyl and tert.-butyl, the term pentyl includes iso-pentyl, neopentyl, etc.

In the abovementioned alkyl groups, unless stated to the contrary, one or more hydrogen atoms may optionally be replaced by other groups. For example these alkyl groups may be substituted fluorine. All the hydrogen atoms of the alkyl group may optionally also be replaced.

By alkyloxy groups, optionally also known as alkoxy groups or —O-alkyl groups, are meant the above-mentioned alkyl groups which are linked by an oxygen bridge. Examples include: methyloxy, ethyloxy, propyloxy, butyloxy, pentyloxy, hexyloxy, heptyloxy and octyloxy, which are optionally also known as methoxy, ethoxy, propoxy etc.

By alkylene bridges or alkylene groups are meant, unless stated otherwise, branched and unbranched alkyl groups with 1 to 6 carbon atoms, for example methylene, ethylene, propylene, isopropylene, n-butylene, iso-butyl, sec. butyl and tert.-butyl etc. bridges. Particularly preferred are methylene, ethylene, propylene and butylene bridges. In the above-mentioned alkylene bridges, unless stated otherwise or additionally defined, 1 to 2 C atoms may optionally be replaced by one or more heteroatoms selected from among oxygen, nitrogen or sulphur.

By alkenyl groups (including those which are a part of other groups) are meant branched and unbranched alkylene groups with 2 to 8 carbon atoms, preferably 2-6 carbon atoms, particularly preferably 2-3 carbon atoms, provided that they have at least one double bond. Examples include: ethenyl, propenyl, butenyl, pentenyl, etc. Unless otherwise specified, the terms propenyl, butenyl etc. used above encompass all the possible isomeric forms. For example the term butenyl includes 1-butenyl, 2-butenyl, 3-butenyl, 1-methyl-1-propenyl, 1-methyl-2-propenyl, 2-methyl-1-propenyl, 2-methyl-2-propenyl and 1-ethyl-1-ethenyl.

In the above-mentioned alkenyl groups, unless otherwise stated, one or more hydrogen atoms may optionally be replaced by other groups. For example these alkyl groups may be substituted by halogen atoms in the form of fluorine. All the hydrogen atoms of the alkenyl group may optionally also be replaced.

Examples of alkenyloxy groups, optionally also known as alkenoxy groups or —O-alkenyl groups, are the above-mentioned alkenyl groups which are linked by an oxygen bridge. Examples include: ethylenoxy, propylenoxy, butylenoxy.

Examples of alkenylene groups (including those which are part of other groups) include branched and unbranched, bridging alkylene groups with 2 to 6 carbon atoms, preferably 2-4 carbon atoms, particularly preferably 2-3 carbon atoms, provided that they have at least one double bond. Examples include: ethenylene, propenylene etc. Unless stated otherwise, the terms propenylene, butenylene etc. used above include all the possible isomeric forms.

Examples of alkynyl groups (including those which are part of other groups) are branched and unbranched alkynyl groups with 2 to 8 carbon atoms, provided that they have at least one triple bond, for example ethynyl, propargyl, butynyl, pentynyl, hexynyl etc., preferably ethynyl or propynyl.

In the above-mentioned alkynyl groups, unless otherwise stated, one or more hydrogen atoms may optionally be replaced by other groups. For example these alkynyl groups may be substituted by fluorine. All the hydrogen atoms of the alkynyl group may optionally also be replaced.

Examples of alkynyloxy groups, optionally also known as alkynoxy groups or —O-alkynyl groups, are the above-mentioned alkynyl groups which are linked by an oxygen bridge.

Examples of alkynylene groups (including those which are part of other groups) are branched and unbranched, bridging alkynyl groups with 2 to 6 carbon atoms, provided that they have at least one triple bond, for example ethynylene, propargylene etc. In the above-mentioned alkynylene groups, unless otherwise stated, one or more hydrogen atoms may optionally be replaced by other groups. Unless stated otherwise, the terms propargylene etc. used above include all the possible isomeric forms.

The term aryl denotes an aromatic ring system with 6 to 14 carbon atoms, preferably 6 or 10 carbon atoms, preferably phenyl or naphthyl, particularly preferably phenyl.

By 5-10-membered heteroaryl groups, which may contain one, two or three heteroatoms selected from among nitrogen, oxygen and sulphur, preferably nitrogen or oxygen, are meant mono- or bicyclic aromatic ring systems which are selected, for example, from among imidazolyl, oxazolyl, isoxazolyl, pyrolyl, pyrazolyl, oxadiazol, pyridyl, pyridazinyl, pyrazinyl, pyrimidinyl, indolyl, quinolinyl, isoquinolinyl, benzimidazolyl, purinyl, pyrimidopyrimidinyl, benzoxazolyl, benzisoxazolyl, pyridopyrimidinyl and pteridinyl.

Examples of cycloalkyl groups are cycloalkyl groups with 3-8 carbon atoms, for example cyclopropyl, cyclobutyl, cyclopentyl, cyclohexyl, cycloheptyl or cyclooctyl, preferably cyclopropyl, cyclopentyl or cyclohexyl. A part from cyclopropyl and cyclobutyl, the above-mentioned cycloalkyl groups may optionally also be partially unsaturated, i.e. they may contain at least one double bond such as for example cyclohexene. The term cylcoalkylene group denotes bridging, double-bonded cycloalkyl groups.

"=O" denotes an oxygen atom linked by a double bond.

Examples of 5-10-membered heterocycloalkyl groups which may contain one, two or three heteroatoms selected from among nitrogen, oxygen and sulphur, preferably nitrogen or oxygen, include, unless stated otherwise in the definitions, for example tetrahydrofuranyl, tetrahydrofuranonyl, γ-butyrolactonyl, α-pyranyl, γ-pyranyl, dioxolanyl, tetrahydropyranyl, dioxanyl, dihydrothiophenyl, thiolanyl, dithiolanyl, pyrrolinyl, pyrrolidinyl, pyrazolinyl, pyrazolidinyl, imidazolinyl, imidazolidinyl, piperidinyl, piperazinyl, morpholinyl, thiomorpholinyl, diazepanyl, oxazinyl, tetrahydrooxazinyl, pyrazolidinyl, preferably morpholinyl, pyrrolidinyl, piperidinyl and piperazinyl.

Halogen generally denotes fluorine, chlorine, bromine or iodine, preferably fluorine, chlorine or bromine, particularly preferably fluorine or chlorine.

The compounds according to the invention may be present in the form of the individual optical isomers, mixtures of the individual enantiomers, diastereomers or racemates, in the form of the tautomers and in the form of the free bases or the corresponding acid addition salts with pharmacologically acceptable acids. By acid addition salts with pharmacologically acceptable acids are meant, for example, the salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate.

Of the above-mentioned acid addition salts the salts of hydrochloric acid, methanesulphonic acid, benzoic acid and acetic acid are particularly preferred according to the invention.

Of the enantiomers and diastereomeric compounds of general formula (I) which may optionally exist, the optical isomers which have the R configuration at the carbon centre carrying the two groups $R^1$ and $R^2$ are preferred according to the invention The group $R^4$, if it is not hydrogen, may be linked in the ortho or meta position in relation to the NH group linked to the pteridinone structure in the compounds of general formula (I). Particularly preferred are those compounds of general formula (I) wherein $R^4$ is in the ortho configuration relative to the above-mentioned NH group. These preferred compounds are characterised by general formula (I')

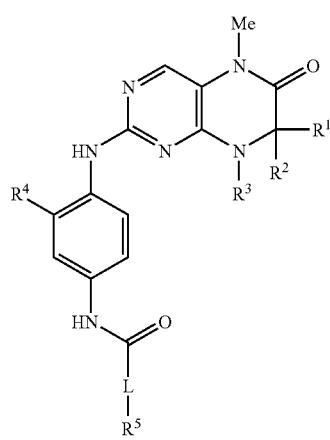

(I')

wherein the groups L, $R^1$, $R^2$, $R^3$, $R^4$ and $R^5$ may have the above-mentioned meanings, optionally in the form of the tautomers, racemates, enantiomers, diastereomers and mixtures thereof, and optionally in the form of the pharmacologically acceptable acid addition salts, solvates and/or hydrates thereof.

The compounds according to the invention may be prepared by synthesis method A described hereinafter, the substituents of general formulae (A1) to (A9) being defined as hereinbefore. This method is to be understood as illustrating the invention without restricting it to the content thereof.

Method A

Step 1A

A compound of formula (A1) is reacted with a compound of formula (A2) to produce a compound of formula (A3) (Diagram 1A). This reaction may be carried out according to WO 0043369 or WO 0043372. Compound (A1) is commercially obtainable, for example from City Chemical LLC, 139 Allings Crossing Road, West Haven, Conn., 06516, USA. Compound (A2) may be prepared by methods described in the literature a) F. Effenberger, U. Burkhart, J. Willfahrt *Liebigs Ann. Chem.* 1986, 314-333. b) T. Fukuyama, C.-K. Jow, M. Cheung, *Tetrahedron Lett.* 1995, 36, 6373-6374. c) R. K. Olsen, *J. Org. Chem.* 1970, 35, 1912-1915. d) F. E. Dutton, B. H. Byung *Tetrahedron Lett.* 1998, 30, 5313-5316. e) J. M. Ranajuhi, M. M. Joullie *Synth. Commun.* 1996, 26, 1379-1384.

Diagram 1A

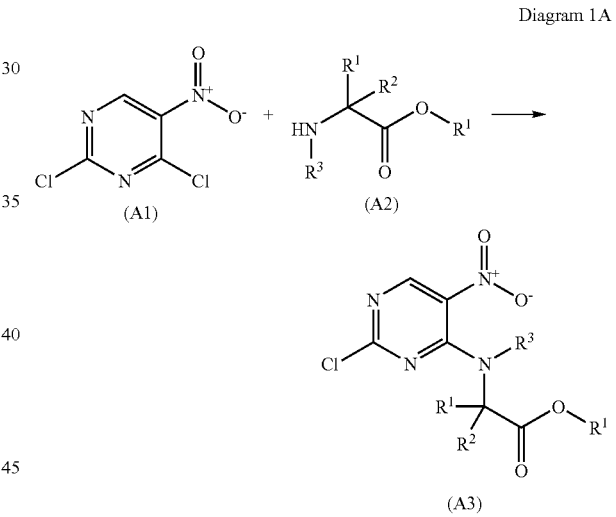

In Step 1A, 1 equivalent of the compound (A1) and 1 to 1.5 equivalents, preferably 1.1 equivalents of a base, preferably potassium carbonate, potassium hydrogen carbonate, sodium carbonate, sodium hydrogen carbonate or calcium carbonate, particularly preferably potassium carbonate, are stirred in a diluent, optionally mixed with water, for example acetone, tetrahydrofuran, diethyl ether, cyclohexane, methylcyclohexane, petroleum ether or dioxane, preferably cyclohexane or diethyl ether.

At a temperature of 0 to 15° C., preferably 5 to 10° C., 1 equivalent of an amino acid of formula (A2) dissolved in an organic solvent, for example acetone, tetrahydrofuran, diethyl ether, cyclohexane or dioxane, is added dropwise. The reaction mixture is heated to a temperature of 18° C. to 30° C., preferably about 22° C., with stirring and then stirred for a further 10 to 24 hours, preferably about 12 hours. Then the diluent is distilled off, the residue is combined with water and the mixture is extracted two to three times with an organic solvent, for example diethyl ether or ethyl acetate, preferably ethyl acetate. The combined organic extracts are dried and the solvent is distilled off. The residue (compound A3) may be used in Step 2 without any prior purification.

Step 2A

The compound (A3) obtained in Step 1A is reduced at the nitro group and cyclised to form the compound of formula (A4) (Diagram 2A).

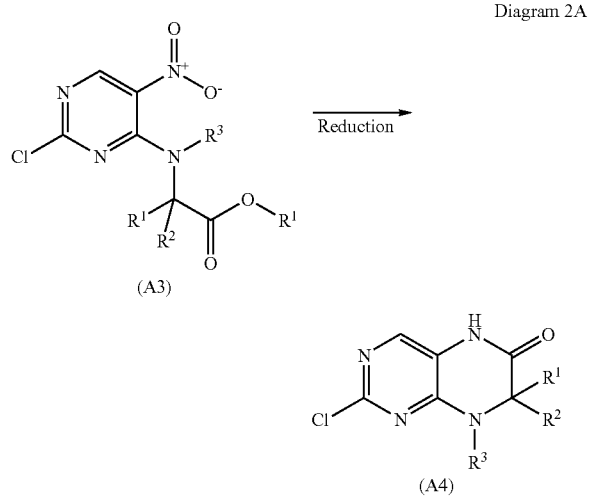

Diagram 2A

In Step 2A 1 equivalent of the nitro compound (A3) is dissolved in an acid, preferably glacial acetic acid, formic acid or aqueous hydrochloric acid, preferably glacial acetic acid, and heated to 50 to 70° C., preferably about 60° C. Then a reducing agent, for example zinc, tin or iron, preferably iron powder, is added until the exothermic reaction has ended and the mixture is stirred for 0.2 to 2 hours, preferably 0.5 hours, at 100 to 125° C., preferably at about 115° C. After cooling to ambient temperature the iron salt is filtered off and the solvent is distilled off. The residue is taken up in a solvent or mixture of solvents, for example ethyl acetate or dichloromethane/methanol 9/1 and semisaturated NaCl solution and filtered through kieselguhr for example. The organic phase is dried and evaporated down. The residue (compound (A4)) may be purified by chromatography or by crystallisation or used as the crude product in Step 3A of the synthesis.

Step 3A

The compound (A4) obtained in Step 2A may be reacted by electrophilic substitution according to Diagram 3A to form the compound of formula (A5).

Diagram 3A

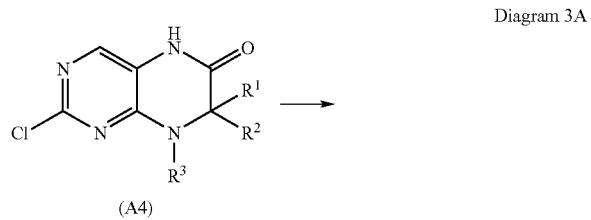

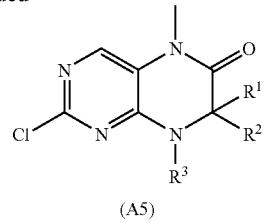

In Step 3A 1 equivalent of the amide of formula (A4) is dissolved in an organic solvent, for example dimethylformamide or dimethylacetamide, preferably dimethylacetamide, and cooled to about −5 to 5° C., preferably 0° C.

Then 0.9 to 1.3 equivalents sodium hydride and 0.9 to 1.3 equivalents of a methylating reagent, for example methyliodide, are added. The reaction mixture is stirred for 0.1-3 hours, preferably about 1 hour, at about 0 to 10° C., preferably at about 5° C., and may optionally be left to stand for a further 12 hours at this temperature range. The reaction mixture is poured onto ice water and the precipitate is isolated. The residue (compound (A5)) may be purified by chromatography, preferably on silica gel, or by crystallisation or used as the crude product in Step 4A of the synthesis.

Step 4A

The amination of the compound (A5) obtained in Step 3A to form the compound of formula (I) (Diagram 4A) may be carried out according to the methods of variants 4.1A known from the literature from (a) M. P. V. Boarland, J. F. W. McOmie *J. Chem. Soc.* 1951, 1218-1221 or (b) F. H. S. Curd, F. C. Rose *J. Chem. Soc.* 1946, 343-348, or 4.2A from (a) Banks *J. Am. Chem. Soc.* 1944, 66, 1131, (b) Ghosh and Dolly *J. Indian Chem. Soc.* 1981, 58, 512-513 or (c) N. P. Reddy and M. Tanaka *Tetrahedron Lett.* 1997, 38, 4807-4810.

Diagram 4A

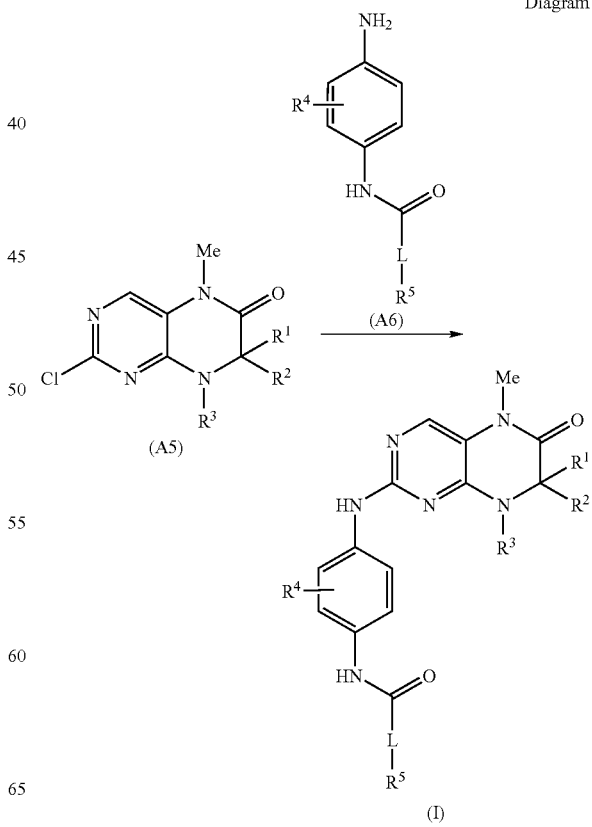

For example in variant 4.1A, 1 equivalent of the compound (A5) and 1 to 3 equivalents, preferably about 1 equivalent of the compound (A6) may be heated without a solvent or with an organic solvent such as for example sulpholane, dimethylformamide, dimethylacetamide, toluene, N-methylpyrrolidone, dimethylsulphoxide, or dioxane, preferably sulpholane over 0.1 to 4 hours, preferably 1 hour, at 100 to 220° C., preferably at about 160° C. After cooling the product (A9) is crystallised by the addition of org. solvents or mixtures of solvents, e.g. diethyl ether/methanol, ethyl acetate, methylene chloride, or diethyl ether, preferably diethyl ether/methanol 9/1, or purified by chromatography.

As can be seen from Diagram 4A, the compounds of formula (A5) are of central importance for the synthesis of the compounds of general formula (I) according to the invention. Accordingly, the present invention also relates to intermediate compounds of general formula (A5)

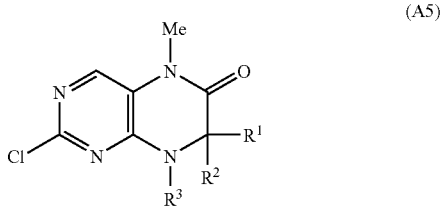

wherein the groups $R^1$, $R^2$ and $R^3$ may have the above-mentioned meanings, optionally in the form of the tautomers, racemates, enantiomers, diastereomers and mixtures thereof, and optionally in the form of the acid addition salts, solvates and/or hydrates thereof.

For example in variant 4.2A, 1 equivalent of the compound (A5) and 1 to 3 equivalents of the compound (A6) are refluxed for 1 to 48 hours, preferably about 5 hours, with acid, for example 1-10 equivalents of 10-38% hydrochloric acid and/or an alcohol such as ethanol, propanol, dioxane or butanol, preferably ethanol, with stirring.

The precipitated product of formula (I) is filtered off and optionally washed with water, dried and crystallised from a suitable org. solvent.

The products of formula (A7) are obtained analogously to the processes described and are converted into the products of formula (I) by further reactions.

Step 5A

After the amination in Step 4A the products of formula (A9) may also be obtained by cleaving an acid- or base-labile group, for example, from compounds of type (A7) or by reduction of a nitro group to the amine (A8) and then reacting it to form amides (A9a), urethanes (A9b) or ureas (A9c) (cf. Diagram 5A).

Variant 5.1A:

For example, 1 equivalent of a compound (A7a) is combined with an acid-labile protective group, for example tert-butyloxycarbonyl with 1-50 equivalents of acid, preferably HCl or trifluoroacetic acid, in an organic solvent e.g. methylene chloride, ether, dioxane or tetrahydrofuran, preferably methylene chloride and stirred for 1 to 24 h at 20-100° C., preferably 20° C. The reaction mixture is separated for example on silica gel or obtained by suitable crystallisation.

Variant 5.2B:

For example, 1 equivalent of a compound (A7b) is dissolved in a solvent e.g. methanol, ethanol, THF, ethyl acetate or water and combined with 0.001 to 0.1 equivalent Pd/C (10%) and hydrogenated with hydrogen for 1-24 h. After filtration of the catalyst the product (A8) is obtained and is optionally purified by silica gel chromatography or by suitable crystallisation.

Diagram 5A

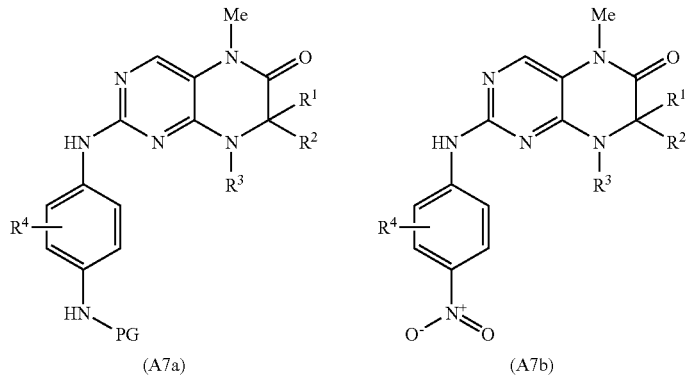

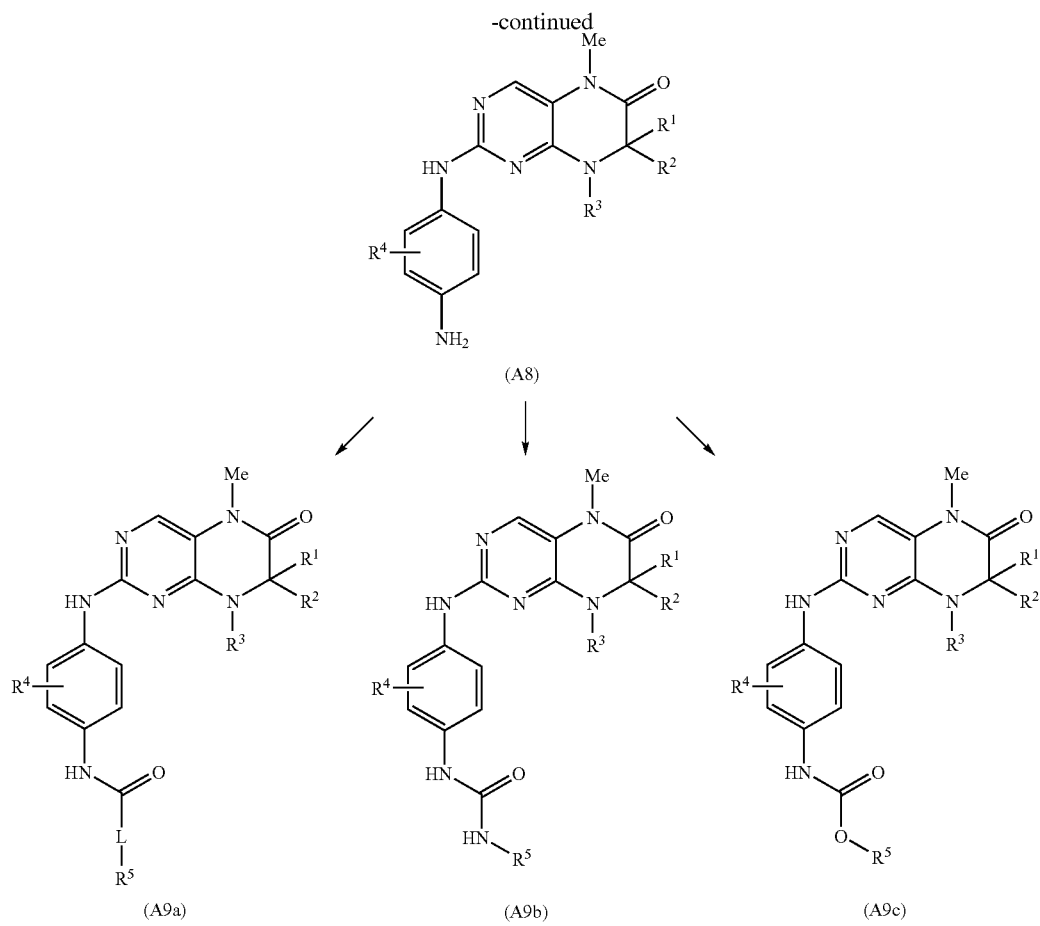

The group PG, as shown in the above diagram at compounds (A7a), may be one of the amino protecting groups known in the art. Suitable methods of cleaving the group PG and hence converting the compounds into the compounds of formula (A8) are known in the art (cf. T. W. Greene, "Protective Groups in Organic Synthesis", 2nd Edition).

The compounds of formulae (A9a), (A9b) and (A9c) shown in Diagram 5A are specific examples of the compounds of formula (I) according to the invention. In the compounds of formula (A9a) L does not represent a group L which is linked to the carbonyl carbon by an —NH or —O— bridge. Rather, these compounds are represented by formulae (A9b) and (A9c).

Preparation of the Amides (A9a)

For example, 1 equivalent of the compound (A8) is dissolved with 1 equivalent of an activating reagent, e.g. O-benzotriazolyl-N,N,N',N'-tetramethyluronium tetrafluoroborate (TBTU) and a base, for example about 1.5 equivalents, diisopropylethylamine (DIPEA) in an organic diluent, for example dichloromethane, tetrahydrofuran, dimethylformamide, N-methylpyrrolidone or dimethylacetamide, preferably dichloromethane or dimethylformamide. After the addition of 1 equivalent of the amine (A 10) the reaction mixture is stirred for 0.1 to 24 hours, preferably about 2 hours at 20° C.

to 100° C. The product of formula (A9a) is obtained for example by crystallisation or chromatographic purification.

Preparation of the Ureas (A9b)

The compounds A9b mentioned in Diagram 5A are compounds wherein L denotes an NH group. The processes described hereinafter may also be used if L represents not only NH but also —NH-alkylene, for example, as will be apparent to the skilled man.

Variant A:

1 equivalent of amine (A8) is dissolved in an organic solvent, for example dichloromethane, THF or dimethylformamide, and a base, for example pyridine, triethylamine or disopropylethylamine, and combined with 1-2 equivalents, preferably 1 equivalent, of 4-nitrophenyl chloroformate. After 1-24 h, preferably 2-5 h, 1 equivalent H$_2$N-L$_n$-R$^5$, dissolved in an organic solvent, is added and the mixture is stirred for 4-24 h at 20° C. The product of formula (A9b) is obtained for example by crystallisation or chromatographic purification.

Variant B:

1 equivalent of the amine (A8) is dissolved together with 1-3 equivalents of an isocyanate in an organic solvent such as dimethylformamide, THF or dimethylacetamide and stirred for 1-24 h at 40-70° C.

After the solvent has been eliminated the product (A9b) is obtained for example by crystallisation or chromatographic purification.

Preparation of the Urethanes (A9c)

The compounds A9c shown in Diagram 5A are compounds wherein L denotes an —O— group. The processes described hereinafter may also be used if L represents not only O but also —O-alkylene, for example, as will be apparent to the skilled man.

1 equivalent of the amine (A7) is dissolved in an organic solvent, such as dichloromethane, dimethylformamide or THF and combined with 1-3 equivalents of base, for example diisopropylethylamine or triethylamine. Subsequently 1-3 equivalents of a chloroformate are added and the mixture is stirred for 1-24 h at 20-60° C. After the solvent has been eliminated the product (A9c) is obtained for example by crystallisation or chromatographic purification.

As can be seen from Diagram 5A, the compounds of formula (A8) are of central importance in the synthesis of the compounds of general formula (I) according to the invention. Accordingly, the present invention also relates to intermediate compounds of general formula (A8)

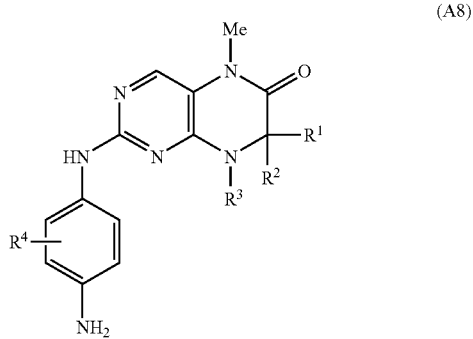
(A8)

wherein the groups $R^1$, $R^2$, $R^3$ and $R^4$ may have the above-mentioned meanings, optionally in the form of the tautomers, racemates, enantiomers, diastereomers and mixtures thereof, and optionally in the form of the acid addition salts, solvates and/or hydrates thereof.

Examples of acid addition salts which may be used particularly include those salts mentioned hereinbefore for the compounds of formula (I) as being pharmacologically acceptable acid addition salts.

As can be seen from Diagram 5A, the compounds of formula (A7a) are also of major importance in the synthesis of the compounds of general formula (I) according to the invention. Accordingly, the present invention also relates to intermediate compounds of general formula (A7a)

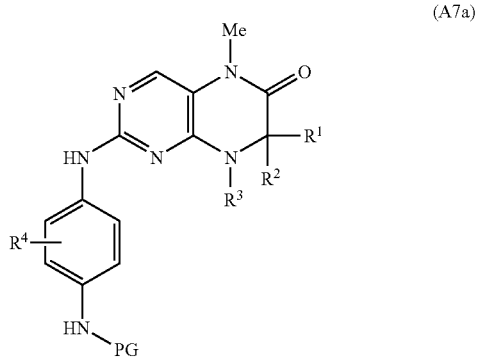
(A7a)

wherein the groups $R^1$, $R^2$, $R^3$ and $R^4$ may have the meanings given above and wherein PG denotes an amino protecting group, optionally in the form of the tautomers, racemates, enantiomers, diastereomers and mixtures thereof, and optionally in the form of the acid addition salts, solvates and/or hydrates thereof.

Preferred are compounds of general formula (A7a), wherein
PG is selected from among tert-butyloxycarbonyl, acetyl, trifluoromethyl, 9-fluoroenylmethyloxycarbonyl, allyloxycarbonyl and benzyloxycarbonyl, preferably tert-butyloxycarbonyl, acetyl and trifluoromethyl, optionally in the form of the tautomers, racemates, enantiomers, diastereomers and mixtures thereof, and optionally in the form of the acid addition salts, solvates and/or hydrates thereof.

As can be seen from Diagram 5A, the compounds of formula (A7b) are also of major importance in the synthesis of the compounds of general formula (I) according to the invention. Accordingly, the present invention also relates to intermediate compounds of general formula (A7b)

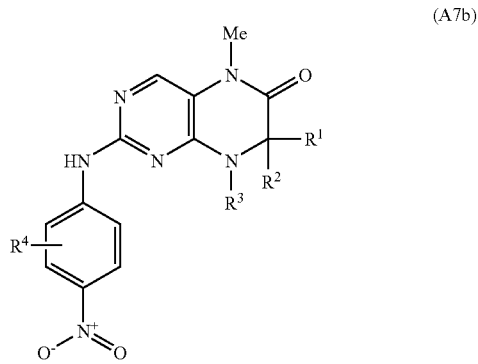
(A7b)

wherein the groups $R^1$, $R^2$, $R^3$ and $R^4$ may have the meanings given above, optionally in the form of the tautomers, racemates, enantiomers, diastereomers and mixtures thereof, and optionally in the form of the acid addition salts, solvates and/or hydrates thereof.

The preparation of a reactant used to synthesise specific intermediates of general formula (A8), the intermediate compounds Z1-Z7, is described below.

Preparation of tert-butyl 4-amino-3-methoxy-phenyl-carbamate

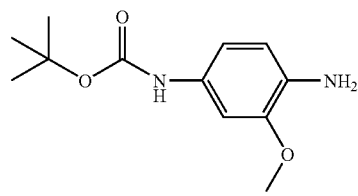

15 g of 4-nitro-3-methoxybenzoic acid was dissolved in 35 g tert-butanol, 16 mL disopropylethylamine and 15 mL toluene, then combined with 17.5 mL diphenylphosphorylazide and refluxed for 7 h. The mixture was then evaporated down and combined with 500 mL ethyl acetate and extracted with 3×200 mL water. The org. phase was dried and the reaction mixture was separated by silica gel chromatography (petroleum ether:ethyl acetate 3:1), and suitable fractions were combined.

Yield: 16.1 g of a compound B1 (bright yellow crystals)

16 g of the compound B1 was dissolved in 400 mL ethanol and reacted with 6 g 10% Pd/C with hydrogen at 20° C. The reaction solution was evaporated down and the solid was triturated with diethyl ether.

Yield: 10.5 g tert-butyl 4-amino-3-methoxy-phenyl-carbamate (colourless crystals)

In order to synthesise Examples 1 to 3 first of all an intermediate compound Z1 is prepared as described below.

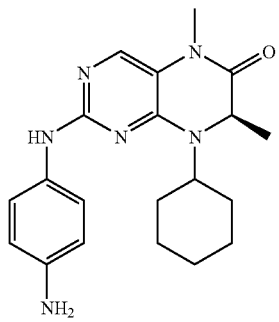

Z1

50.0 g D-alanine methylester x HCl and 49.1 g cyclohexanone were placed in 300 mL dichloromethane and then combined with 41.0 g sodium acetate and 159.0 g sodium triacetoxyborohydride. The mixture was stirred overnight and then 300 mL of 10% sodium hydrogen carbonate solution were added. The aqueous phase was extracted with dichloromethane. The combined organic phases were washed with 10% sodium hydrogen carbonate solution, dried over $Na_2SO_4$ and evaporated down.

Yield: 72.5 g of a compound Z1a (clear liquid)

72.5 g of the compound Z1a were placed in 500 mL water and 76.6 g (0.39 mol) 2,4-dichloro-5-nitropyrimidine in 500 mL diethyl ether were added. At a temperature of −5° C. 100 mL 10% potassium hydrogen carbonate solution were added dropwise. The mixture was stirred for 3 h at −5° C. and for a further 12 h at ambient temperature. The organic phase was separated off and dried over $Na_2SO_4$. During evaporation the product crystallises out.

Yield: 48.0 g of a compound Z1b (yellow crystals)

48.0 g of the compound Z1b were dissolved in 350 mL glacial acetic acid and heated to 60° C. 47.5 g iron powder were added batchwise, while the temperature rose to 105° C. The reaction mixture was stirred for three hours at 80° C., then filtered hot through cellulose and evaporated down. The residue was stirred in water and ethyl acetate, suction filtered and the light grey precipitate was washed with ethyl acetate. The filtrate was washed with dilute ammonia and water, the organic phase was dried over $Na_2SO_4$, filtered through activated charcoal and evaporated down.

Yield: 29.5 g of a compound Z1c (light grey crystals)

32.1 g of the compound Z1c were placed in 300 mL dimethylacetamide and combined with 13 mL (0.2 mol) methyliodide. At −5° C. 6.4 g (0.16 mol) sodium hydride were added batchwise as a 60% dispersion in mineral oil. After 2 h the reaction mixture was poured onto 800 mL ice water. The precipitate formed was suction filtered and washed with petroleum ether.

Yield: 33.0 g of a compound Z1d (beige crystals)

8 g of Z1d were refluxed for 12 h together with 5.54 g 4-trifluoracetyl-p-phenylenediamine in a solution of 40 mL ethanol, 40 mL water and 10 mL hydrochloric acid. The ethanol was then eliminated in vacuo, the reaction mixture was cooled and the precipitate formed was filtered off. The mother liquor was evaporated down and the residue was triturated with ethanol.

Yield: 5.86 g of the intermediate compound Z1 as a beige solid

In order to synthesise Examples 17 to 20 first of all an intermediate compound Z2 is prepared as described below.

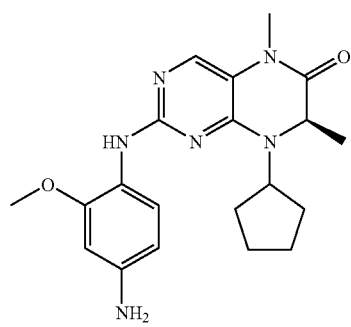

Z2

A solution of 128.2 g (0.83 mol) D-alanine ethylester x HCl and 71.5 g (0.85 mol) cyclopentanone in 1500 mL dichloromethane was combined with 70.1 (0.85 mol) sodium acetate and 265.6 g (1.25 mol) sodium triacetoxyborohydride. The reaction mixture was stirred for 12 h and then poured into 1.5 L of a 10% sodium hydrogen carbonate solution. The aqueous phase was extracted with dichloromethane. The combined organic phases were dried over $Na_2SO_4$ and evaporated down.

Yield: 143.4 g of a compound Z2a (colourless oil)

66.0 g of the compound Z2a were placed in 500 mL water and combined with 85.0 g (0.44 mol) 2,4-dichloro-5-nitropyrimidine in 500 mL diethyl ether. At −5° C. 100 mL 10% potassium hydrogen carbonate solution were added dropwise and the reaction mixture was stirred for 48 h at ambient temperature. The aqueous phase was extracted with diethyl ether, the combined organic phases were dried over $Na_2SO_4$ and evaporated down. The dark red solid was extracted with petroleum ether and suction filtered.

Yield: 88.0 g of a compound Z2b (yellow crystals)

88.0 g of the compound Z2b were dissolved in 1000 mL glacial acetic acid and at 60° C. 85 g iron powder were added batchwise, while the temperature rose to 110° C. The mixture was stirred for 1 h at 60° C., then suction filtered hot through cellulose and evaporated down. The brown solid was stirred with 700 mL water and suction filtered.

Yield: 53.3 g of a compound Z2c (light brown crystals)

53.3 g of the compound Z2c were dissolved in 300 mL dimethylacetamide and combined with 13 mL (0.21 mol) methyl iodide. At −5° C. 5.0 g (0.21 mol) sodium hydride were added batchwise as 60% dispersion in mineral oil. After 12 h the reaction mixture was poured onto 1000 mL ice water and the precipitate formed was suction filtered.

Yield: 40.0 g of a compound Z2d (colourless crystals)

1.95 g of Z2d and 1.66 g tert-butyl 4-amino-3-methoxy-phenyl-carbamate were melted together at 120° C. for 4.5 h. After cooling the reaction mixture was dissolved in dichloromethane and extracted 1× with potassium carbonate solution and 2× with water. After drying the org. phase the mixture was separated by silica gel chromatography (eluant 99:1, $CH_2Cl_2$:MeOH) and the product fractions were combined.

Yield: 1.76 g of the compound Z2e (brown solid)

1.75 g of Z2e was dissolved in 100 mL methylene chloride and the solution was combined with 20 mL trifluoroacetic acid. After 12 h stirring at 25° C. the reaction mixture was added to semiconcentrated ammonia solution while being cooled and the org. phase was separated off and extracted with water. After elimination of the solvent the mixture was dissolved in acetone and combined with ethereal HCl. The precipitate formed was filtered off and dried.

Yield: 1.32 g of the intermediate compound Z2

In order to synthesise Examples 13 and 21 to 23 first of all an intermediate compound Z3 is prepared as described below.

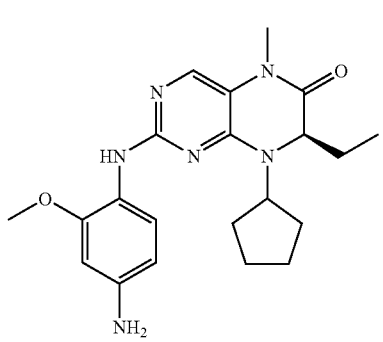

Z3

54.0 g (0.52 mol) D-2-aminobutyric acid were suspended in 540 mL methanol and 132 g (1.1 mol) thionyl chloride were slowly added while cooling with ice. The mixture was refluxed for 1.5 h and then evaporated down. The oil remaining was combined with 540 mL tert-butylmethylether and the colourless crystals obtained were suction filtered.

Yield: 78.8 g of a compound Z3a (colourless crystals)

74.2 g of the compound Z3a and 43.5 mL (0.49 mol) cyclopentanone were dissolved in 800 mL dichloromethane. After the addition of 40.0 g (0.49 mol) sodium acetate and 150.0 g (0.71 mol) sodium triacetoxyborohydride at 0° C. the mixture was stirred for 12 h at ambient temperature and then 500 mL 20% sodium hydrogen carbonate solution were added. The aqueous phase was extracted with dichloromethane. The combined organic phases were washed with water, dried over $MgSO_4$ and evaporated down.

Yield: 85.8 g of a compound Z3b (light yellow oil)

40.0 g of the compound Z3b and 30.0 g (0.22 mol) potassium carbonate were suspended in 600 mL acetone and while cooling with ice combined with 45.0 g (0.23 mol) 2,4-dichloro-5-nitropyrimidine in 200 mL acetone. After 12 h a further 5.0 g of 2,4-dichloro-5-nitropyrimidine were added and the mixture was stirred for 3 h. The reaction mixture was evaporated down, taken up in 800 mL ethyl acetate and 600 mL water and the aqueous phase was extracted with ethyl acetate. The combined organic phases were washed with water, dried over $MgSO_4$ and evaporated down.

Yield: 75.0 g of a compound Z3c (brown oil)

100 g of the compound Z3c were dissolved in 650 mL glacial acetic acid and at 70° C. 20 g iron powder were added batchwise. The mixture was stirred for 1 h at 70° C., then for 1.5 h at 100° C. and then filtered hot through kieselguhr. The reaction mixture was evaporated down, taken up in methanol/dichloromethane, applied to silica gel and purified by Soxhlet extraction with ethyl acetate. The solvent was removed and the residue was stirred with methanol.

Yield: 30.0 g of a compound Z3d (light brown crystals)

25.0 g of the compound Z3d and 6.5 mL (0.1 mol) methyl iodide were placed in 250 mL dimethylacetamide and at −10° C. 3.8 g (0.95 mol) sodium hydride were added as a 60% dispersion in mineral oil. The mixture was stirred for 20 min. at 0° C., then 30 min. at ambient temperature and finally ice was added. The reaction mixture was evaporated down and combined with 300 mL water. The precipitate formed was suction filtered and washed with petroleum ether.

Yield: 23.0 g of a compound Z3e (colourless solid)

1.5 g Z3e and 1.22 g tert-butyl 4-amino-3-methoxy-phenyl-carbamate were melted together at 120° C. for 5 h. After cooling the reaction mixture was dissolved in dichloromethane and extracted 2× with potassium carbonate solution and 2× with water. After drying the org. phase the mixture was separated by silica gel chromatography (eluant 99:1, $CH_2Cl_2$:MeOH) and the product fractions were combined.

Yield: 0.92 g of a compound Z3f (light brown crystals)

0.92 g Z3f were dissolved in 100 mL methylene chloride, 15 mL trifluoroacetic acid were added and the mixture was stirred for 3 h at 20° C. Then the solution was added to a mixture of 10 g ice and 100 mL of a 25% ammonia solution and the org. phase was extracted with water and evaporated down after drying. The residue was dissolved in acetone and combined with ethereal HCl. The crystals precipitated were filtered off and dried.

Yield: 0.54 g of the intermediate compound Z3 (light brown crystals)

In order to synthesise Examples 7 to 9 and 15 first of all an intermediate compound Z4 is prepared as described below.

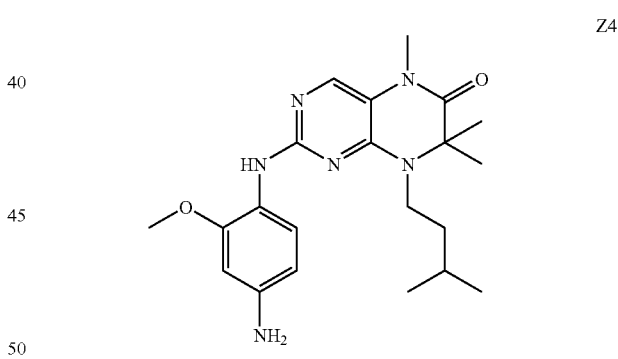

Z4

A mixture of 73.4 mL ethyl 2-bromoisobutyrate, 87.1 mL 3-methyl-1-butylamine, 82.5 g (0.6 mol) sodium iodide and 76.0 g (0.6 mol) potassium carbonate in 1000 mL ethyl acetate was refluxed for 3 days. Any salts present were filtered off and the filtrate was evaporated down.

Yield: 97.0 g of a compound Z4a (red oil)

49.0 g 2,4-dichloro-5-nitropyrimidine and 38.3 g potassium carbonate were suspended in 500 mL acetone and at 0° C. combined with 93.0 g of the compound Z4a in 375 mL acetone. The reaction mixture was stirred overnight at ambient temperature, filtered and evaporated down. The residue dissolved in ethyl acetate was washed with water and the organic phase was dried over $MgSO_4$ and evaporated down.

Yield: 102.7 g of a compound Z4b (brown oil)

22.7 g of the compound Z4b were dissolved in 350 mL glacial acetic acid and at 60° C. 17.4 g of iron powder were added batchwise. After the addition had ended the mixture was refluxed for 0.5 h, filtered hot and evaporated down. The residue was taken up in 200 mL dichloromethane/methanol (9:1) and washed with sodium chloride solution. The organic phase was suction filtered through kieselguhr, dried over MgSO₄, evaporated down and separated by column chromatography (eluant: ethyl acetate/cyclohexane 1:1) and suitable fractions were combined.

Yield: 1.9 g of a compound Z4c (colourless crystals)

1.9 g of the compound Z4c were dissolved in 32 mL dimethylacetamide and while cooling with ice combined with 0.3 g (7 mmol) of sodium hydride as a 60% dispersion in mineral oil. After 10 min. 0.5 mL (7 mmol) of methyl iodide were added and the mixture was stirred for 3 h at ambient temperature. The reaction mixture was evaporated down and combined with water. The precipitate formed was suction filtered and washed with petroleum ether.

Yield: 1.6 g of a compound Z4d (colourless crystals)

1.5 g of Z4d and 1.21 g tert-butyl 4-amino-3-methoxy-phenyl-carbamate were melted together at 120° C. for 4.5 h. After cooling the reaction mixture was dissolved in dichloromethane and extracted 1× with potassium carbonate solution and 1× with water. After drying the org. phase the mixture was separated by silica gel chromatography (eluant 98:2, CH₂Cl₂:MeOH) and the product fractions were combined.

Yield: 1.12 g of a compound Z4e (light brown solid)

1.12 g Z4e was dissolved in 100 mL methylene chloride, 18 mL trifluoroacetic acid were added and the mixture was stirred for 12 h at 20° C. Then the solution was added to a semiconc. ammonia solution and the org. phase was extracted with water and evaporated down.

Yield: 0.84 g of the intermediate compound Z4 (beige solid)

The following intermediates were prepared analogously to the syntheses described above:

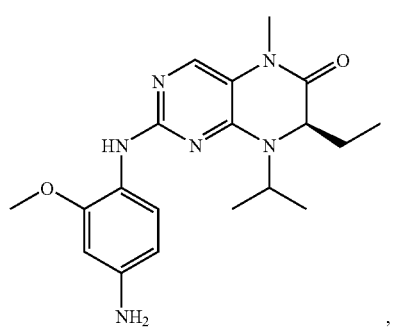

Z5

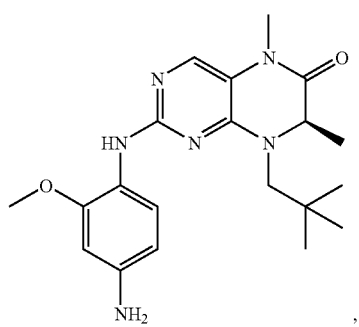

Z6

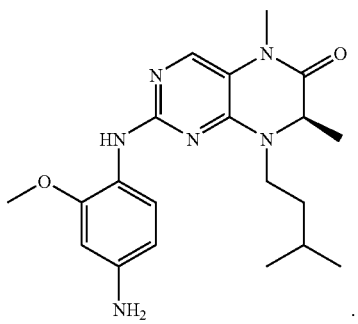

Z7

The preparation of some reactants used to synthesise the products is described hereinafter.

The following acid may be obtained for example by the following method known from the literature:

1-methyl-piperidine-4-carboxylic acid

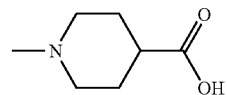

Gray, Allan P.; Platz, Robert D.; Henderson, Theresa R.; Chang, Timothy C. P.; Takahashi, Kazuyuki; Dretchen, Kenneth L, Journal of Medicinal Chemistry (1988), 31(4), 807-14.

4-morpholinyl-4-yl-cyclohexanecarboxylic acid chloride

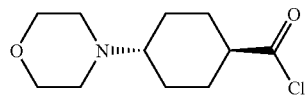

Z8

450 mg of methyl 4-amino-cyclohexanecarboxylate*hydrochloride (e.g. obtained according to the following literature: Johnston, Thomas P.; McCaleb, George S.; Clayton, Sarah D.; Frye, Jerry L.; Krauth, Charles A.; Montgomery, John A. Journal of Medicinal Chemistry (1977), 20(2), 279-90), 0.345 mL bis-(2-chloroethyl)ether and 1.4 g potassium carbonate were dissolved in 4 mL dimethylformamide and heated together with 50 mg potassium iodide to 100° C. for 3 h. Then 30 mL water were added and the mixture was neutralised with acetic acid. The aqueous phase was extracted with dichloromethane. After evaporation the mixture was separated by silica gel chromatography (methylene chloride:MeOH 15:1) and the suitable fractions were combined.

Yield: 259 mg of a product Z8a 233.3 mg Z8a was dissolved in 5 mL 1M sodium hydroxide solution and 4 mL methanol and stirred for 12 h at 20° C. After elimination of the methanol the mixture was neutralised with 1M hydrochloric acid, evaporated down completely, the mixture was suspended in methanol and the product was filtered off. It was then suspended in ethanol again, the insoluble residue was filtered off and the mother liquor was evaporated down.

Yield: 206 mg of the acid Z8b (white solid)

206 mg of Z8b was refluxed in 150 µL thionyl chloride and 5 mL toluene for 3 h. The mixture was then evaporated to dryness, the precipitate was stirred overnight with ether and filtered off.

Yield: 204 mg of the intermediate Z8

The compound Z8 is not yet known in the art. In view of its importance as a starting material for numerous compounds of formula (I) according to the invention, the present invention further relates to the compound of formula Z8

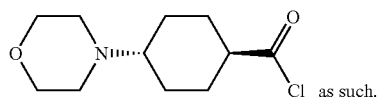

Z8 as such.

trans-4-(4-cyclopropylmethyl-piperazin-1-yl)-cyclohexylamine

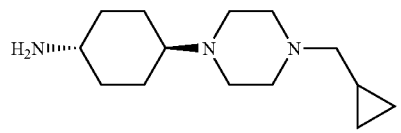

Z9

9.8 g N,N-dibenzyl-4-amino-cyclohexanone was dissolved in 100 mL dichloromethane and stirred with 5.6 g N-cyclopropylmethylpiperazine and 8.5 g NaBH(OAc)$_3$ for 12 h at RT. Then the mixture was combined with water and potassium carbonate, the org. phase was separated off, dried and the solvent was eliminated in vacuo. The residue was separated off using a silica gel column (approx. 50 mL silica gel, approx. 3 L ethyl acetate 95/methanol 5+0.25% conc. ammonia). The suitable fractions were evaporated down in vacuo. The desired compound was crystallised from ethanol+ conc. HCl.

Yield: 8.5 g of the compound Z9a.

8.5 g of Z14a were dissolved in 170 mL MeOH and hydrogenated on 1.7 g Pd/C (10%) at 30-50° C. The solvent was eliminated in vacuo and the residue was crystallised from ethanol and conc. HCl.

Yield: 4.4 g of the intermediate Z9.

trans-4-(2,6-dimethyl-morpholin-4-yl)-cyclohexylamine

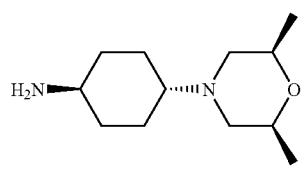

Z10

110 mL benzylamine and 156 g cyclohexanedione monoethylene ketal were heated in 800 mL toluene using a water separator. Then the solution was evaporated down and the reaction mixture was taken up in 1000 mL ethanol and combined batchwise with a total of 23 g sodium borohydride while being cooled to 15° C. After 12 h the reaction solution was evaporated down and the residue was combined with 500 mL water, extracted 2× with 400 mL ether, then the org. phase was washed with water, dried, evaporated down and the residue was distilled under a high vacuum.

Yield: 208 g of a product Z10a 208 g Z10a were heated together with 114 g benzyl chloride, 138 g potassium carbonate and 14 g potassium iodide in 400 mL N-methylpyrrolidone for 24 h at 80° C. Subsequently 5 L water was added and the solid formed was filtered off and washed with water again. Then it was dissolved in 1 L methylene chloride, the org. phase was dried and evaporated down. The residue was crystallised from methanol.

Yield: 260 g of a product Z10b 260 g Z10b was dissolved in 400 mL water and 100 mL 37% HCl and stirred for 4 h at 100°. After cooling the mixture was made alkaline with potassium carbonate and the crystals precipitated were filtered off and washed with water. The solid was dissolved in dichloromethane, the org. phase was dried and evaporated down. The residue was recrystallised from petroleum ether.

Yield: 216 g of a product Z10c 44 g Z10c and 23 g cis-2,6-dimethylmorpholine were refluxed in 100 mL toluene and 0.1 mL methanesulphonic acid for 2 h using a water separator. The mixture was then cooled, the solvent was eliminated, and 400 mL ethanol were added and 8 g sodium borohydride were added batchwise. The reaction temperature rose to 45° C., then after the exothermic reaction had died down the mixture was heated to 60° C. for 3 h, cooled and combined with 400 mL water and, while being cooled, combined with 300 mL 2N HCl. Subsequently ethanol was added and the mixture was combined with 400 mL 2N NaOH. The residue was extracted with 2×300 mL dichloromethane. The org. phase was dried, evaporated down and combined with 100 mL methanol, the solid was filtered off and the mother liquor was evaporated down. The residue was separated by silica gel chromatography and suitable fractions were combined.

Yield: 35.2 of a product Z10d 35 g Z10d was dissolved in 400 mL methanol and hydrogenated with 7 g Pd/C (10%) at 50 psi hydrogen and 50° C. for 4 h. Subsequently the mixture was evaporated down, suspended in 200 mL ethanol, 10 mL 37% hydrochloric acid were added dropwise, the mixture was stirred for 30 minutes in the ice bath and the crystals were filtered off and washed with cold ether and ethanol.

Yield: 24 g of the intermediate product Z10

The new compounds of general formula (I) may be synthesised analogously to the following synthesis examples. These Examples are however intended only as possible methods to illustrate the invention more fully without limiting it to their content.

SYNTHESIS OF THE EXAMPLES

Example 1

0.1 g Z1, 82 mg nicotinic acid chloride and 0.2 mL triethylamine were stirred for 1 h in 10 mL dichloromethane at 20° C., then the mixture was extracted with water and the dried org. phase was evaporated down. The residue was crystallised from methanol and filtered off.

Yield: 0.025 g of a white solid

Example 7

0.1 g Z4, 23 μL cyclopropylcarboxylic acid chloride and 0.15 mL triethylamine were stirred for 2 h in 2 mL dichloromethane at 20° C., then the org. phase was extracted with 20 mL 5% aqueous potassium carbonate solution. The org. phase was evaporated down and the mixture was separated by silica gel chromatography. The suitable fractions were combined, evaporated down and the residue was crystallised from ethyl acetate and petroleum ether.

Yield: 0.071 g white crystals

Example 16

0.1 g Z6, 65 mg 1-benzyl-piperidine-4-carboxylic acid chloride and 0.2 mL triethylamine were stirred for 2 h in 2 mL dichloromethane at 20° C., then the org. phase was extracted with 20 mL 5% aqueous potassium carbonate solution. The org. phase was evaporated down and the mixture was separated by silica gel chromatography. The suitable fractions were combined, evaporated down and the residue was crystallised from ethyl acetate and petroleum ether.

Yield: 0.067 g white crystals

Example 23

0.1 g Z3, 76 mg 1-methyl-piperidine-4-carboxylic acid chloride and 0.3 mL triethylamine were stirred for 2 h in 2 mL dichloromethane at 20° C., then the org. phase was extracted with 20 mL 5% aqueous potassium carbonate solution. The org. phase was evaporated down and the mixture was separated by silica gel chromatography. The suitable fractions were combined, evaporated down and the residue was crystallised from ethyl acetate and petroleum ether.

Yield: 0.064 g white crystals

Example 27

0.2 g Z5 is dissolved in 2 mL dichloromethane, 0.5 mL THF and 0.5 mL pyridine, then 144 mg 4-nitrophenyl chloroformate, dissolved in 1 mL dichloromethane, was added. After 3 h, 111 mg of 1-methyl-piperidin-4-ylamine dissolved in 0.5 mL dichloromethane were added and the mixture was stirred for 12 h at 20° C. Then dichloromethane was added and the mixture was extracted 3× with water. The dried org. phase is evaporated down and the mixture is separated by silica gel chromatography. Suitable fractions were combined, evaporated down and crystallised from ethyl acetate and petroleum ether.

Yield: 97 mg as a grey solid

The compounds of formula (I) listed in Table 1, inter alia, are obtained analogously to the methods described hereinbefore.

The present invention relates, in particularly preferred embodiments, to the compounds of formula (I), as listed in Table 1, per se, optionally in the form of the tautomers, racemates, enantiomers, diastereomers and mixtures thereof, and optionally in the form of the pharmacologically acceptable acid addition salts, solvates and/or hydrates thereof.

TABLE 1

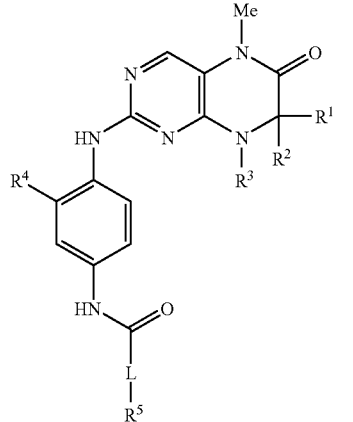

(I')

| Example | Config. —C*($R^1R^2$)— | —$R^1$ | —$R^2$ | —$R^3$ | —$R^4$ | —L— | —$R^5$ | m.p. [° C.] |
|---|---|---|---|---|---|---|---|---|
| 1 | R | —H | —Me | cyclohexyl | —H | — | pyridyl | 276 (decomp.) |
| 2 | R | —H | —Me | cyclohexyl | —H | — | N-methylpiperidyl | 219 |
| 3 | R | —H | —Me | cyclohexyl | —H | — | cyclopropyl | 211 |

TABLE 1-continued (I')

| Example | Config. —C*(R¹R²)— | —R¹ | —R² | —R³ | —R⁴ | —L— | —R⁵ | m.p. [° C.] |
|---|---|---|---|---|---|---|---|---|
| 4 | R | —H | —Me | CH(Me)CH₂CH₂Me (2-pentyl) | —OMe | — | cyclopropyl | 178 |
| 5 | R | —H | —Me | CH(Me)CH₂CH₂Me | —OMe | — | pyridin-3-yl | 171 |
| 6 | R | —H | —Me | CH(Me)CH₂CH₂Me | —OMe | — | 1-methylpiperidin-4-yl | 88 |
| 7 | — | —Me | —Me | CH(Me)CH₂CH₂Me | —OMe | — | cyclopropyl | 148 |
| 8 | — | —Me | —Me | CH(Me)CH₂CH₂Me | —OMe | — | pyridin-3-yl | 152 |
| 9 | — | —Me | —Me | CH(Me)CH₂CH₂Me | —OMe | — | 1-methylpiperidin-4-yl | 205 |
| 10 | R | —H | —Me | CH₂C(Me)₃ (neopentyl) | —OMe | — | cyclopropyl | 157 |
| 11 | R | —H | —Me | CH₂C(Me)₃ | —OMe | — | pyridin-3-yl | 156 |
| 12 | R | —H | —Me | CH₂C(Me)₃ | —OMe | — | 1-methylpiperidin-4-yl | 161 |
| 13 | R | —H | —Et | cyclopentylmethyl | —OMe | — | 1-benzylpiperidin-4-yl | 120 |

TABLE 1-continued
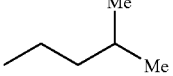
(I')
| Example | Config. —C*(R¹R²)— | —R¹ | —R² | —R³ | —R⁴ | —L— | —R⁵ | m.p. [° C.] |
|---|---|---|---|---|---|---|---|---|
| 14 | R | —H | —Me | 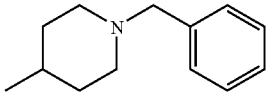 | —OMe | — | 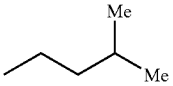 | 180 |
| 15 | — | —Me | —Me | 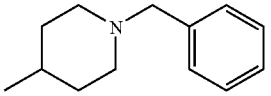 | —OMe | — | 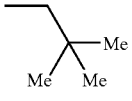 | 180 |
| 16 | R | —H | —Me | 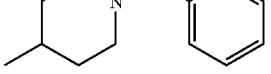 | —OMe | — | 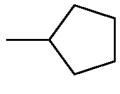 | 136 |
| 17 | R | —H | —Me | 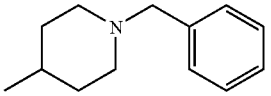 | —OMe | — | 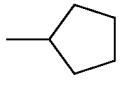 | 135 |
| 18 | R | —H | —Me | 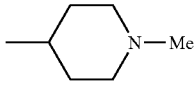 | —OMe | — | 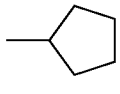 | 230 |
| 19 | R | —H | —Me | 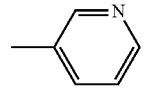 | —OMe | — | 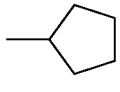 | 197 |
| 20 | R | —H | —Me |  | —OMe | — | 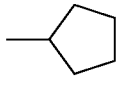 | 204 |
| 21 | R | —H | —Et |  | —OMe | — | 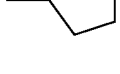 | 136 |
| 22 | R | —H | —Et | 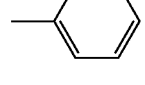 | —OMe | — | 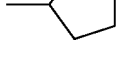 | 170 |
| 23 | R | —H | —Et | 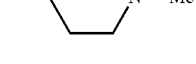 | —OMe | — |  | 112 |

TABLE 1-continued (I')

Structure: pteridinone core with Me on N5, R¹/R²/R³ substituents, linked via HN to a phenyl ring bearing R⁴, which has an NH-C(=O)-L-R⁵ amide substituent.

| Example | Config. —C*(R¹R²)— | —R¹ | —R² | —R³ | —R⁴ | —L— | —R⁵ | m.p. [° C.] |
|---|---|---|---|---|---|---|---|---|
| 24 | R | —H | —Et | CH(Me)(Me) (isopropyl) | —OMe | — | cyclopropyl | 112 |
| 25 | R | —H | —Et | CH(Me)(Me) | —OMe | — | 4-(N-Me)piperidinyl | 134 |
| 26 | R | —H | —Et | CH(Me)(Me) | —OMe | — | trans-4-morpholinocyclohexyl (Me wedge) | 157 |
| 27 | R | —H | —Et | CH(Me)(Me) | —OMe | —NH— | 4-(N-Me)piperidinyl | 158 |
| 28 | R | —H | —Et | CH(Me)(Me) | —OMe | —NH— | cyclopropyl | 142 |
| 29 | R | —H | —Et | CH(Me)(Me) | —OMe | —NH— | trans-4-[4-(cyclopropylmethyl)piperazin-1-yl]cyclohexyl | 148 |
| 20 | R | —H | —Et | CH(Me)(Me) | —OMe | —NH— | trans-4-(2,6-dimethylmorpholin-4-yl)cyclohexyl | 164 |

As has been found, the compounds of general formula (I) are characterised by their many possible applications in the therapeutic field. Particular mention should be made of those applications for which the inhibition of specific cell cycle kinases, particularly their inhibiting effect on the proliferation of cultivated human tumour cells, and also on the proliferation of other cells, such as e.g. endothelial cells, plays a part.

As demonstrated by DNA staining followed by FACS analysis, the inhibition of proliferation brought about by the compounds according to the invention is mediated by the arrest of the cells above all in the G2/M phase of the cell cycle. The cells arrest, depending on the cells used, for a specific length of time in this cell cycle phase before programmed cell death is initiated. An arrest in the G2/M phase of the cell cycle is initiated e.g. by the inhibition of specific cell cycle kinases.

On the basis of their biological properties the compounds of general formula I according to the invention, their isomers and the physiologically acceptable salts thereof are suitable for treating diseases characterised by excessive or anomalous cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours; skin diseases (e.g. psoriasis); bone diseases and; cardiovascular diseases (e.g. restenosis and hypertrophy). They are also useful for protecting proliferating cells (e.g. hair, intestinal, blood and progenitor cells) from DNA damage caused by radiation, UV treatment and/or cytostatic treatment (Davis et al., 2001). The new compounds may be used for the prevention, short- or long-term treatment of the above-mentioned diseases, also in combination with other active substances used for the same indications, e.g. cytostatics, hormones or antibodies.

The activity of the compounds according to the invention was determined in the PLK1 inhibition assay, in the cytotoxicity test on cultivated human tumour cells and/or in a FACS analysis, e.g. on HeLa S3 cells. In both test methods the compounds exhibited a good to very good activity, i.e. for example an $EC_{50}$ value in the HeLa S3 cytotoxicity test of less than 5 μmol/L, generally less than 1 μmol/L, and an $IC_{50}$ value in the PLK1 inhibition assay of less than 1 μmol/L.

PLK-1 Kinase Assay

Enzyme Preparation:

Recombinant human PLK1 enzyme linked to GST at its N-terminal end is isolated from insect cells infected with baculovirus (Sf21). Purification is carried out by affinity chromatography on glutathione sepharose columns.

$4 \times 10^7$ Sf21 cells (*Spodoptera frugiperda*) in 200 ml of Sf-900 II Serum free insect cell medium (Life Technologies) are seeded in a spinner flask. After 72 hours' incubation at 27° C. and 70 rpm, $1 \times 10^8$ Sf21 cells are seeded in a total of 180 ml medium in a new spinner flask. After another 24 hours, 20 ml of recombinant Baculovirus stock suspension are added and the cells are cultivated for 72 hours at 27° C. at 70 rpm. 3 hours before harvesting, okadaic acid is added (Calbiochem, final concentration 0.1 μM) and the suspension is incubated further. The cell number is determined, the cells are removed by centrifuging (5 minutes, 4° C., 800 rpm) and washed 1× with PBS (8 g NaCl/l, 0.2 g KCl/l, 1.44 g $Na_2HPO_4$/l, 0.24 g $KH_2PO4$/l). After centrifuging again the pellet is flash-frozen in liquid nitrogen. Then the pellet is quickly thawed and resuspended in ice-cold lysis buffer (50 mM HEPES pH 7.5, 10 mM $MgCl_2$, 1 mM DTT, 5 μg/ml leupeptin, 5 μg/ml aprotinin, 100 μM NaF, 100 μM PMSF, 10 mM β-glycerolphosphate, 0.1 mM $Na_3VO_4$, 30 mM 4-nitrophenylphosphate) to give $1 \times 10^8$ cells/17.5 ml. The cells are lysed for 30 minutes on ice. After removal of the cell debris by centrifugation (4000 rpm, 5 minutes) the clear supernatant is combined with glutathione sepharose beads (1 ml resuspended and washed beads per 50 ml of supernatant) and the mixture is incubated for 30 minutes at 4° C. on a rotating board. Then the beads are washed with lysis buffer and the recombinant protein is eluted from the beads with 1 ml elution buffer/ml resuspended beads (elution buffer: 100 mM Tris/HCl pH=8.0, 120 mM NaCl, 20 mM reduced glutathione (Sigma G-4251), 10 mM $MgCl_2$, 1 mM DTT). The protein concentration is determined by Bradford Assay.

Assay Procedure

The following components are combined in a well of a 96-well round-bottomed dish (Greiner bio-one, PS Microtitre plate No. 650101):

- 10 μl of the compound to be tested in variable concentrations (e.g. beginning at 300 μM, and dilution to 1:3) in 6% DMSO, 0.5 mg/ml casein (Sigma C-5890), 60 mM β-glycerophosphate, 25 mM MOPS pH=7.0, 5 mM EGTA, 15 mM $MgCl_2$, 1 mM DTT
- 20 μl substrate solution (25 mM MOPS pH=7.0, 15 mM $MgCl_2$, 1 mM DTT, 2.5 mM EGTA, 30 mM β-glycerophosphate, 0.25 mg/ml casein)
- 20 μl enzyme dilution (1:100 dilution of the enzyme stock in 25 mM MOPS pH=7.0, 15 mM $MgCl_2$, 1 mM DTT)
- 10 μl ATP solution (45 μM ATP with $1.11 \times 10^6$ Bq/ml gamma-P33-ATP).

The reaction is started by adding the ATP solution and continued for 45 minutes at 30° C. with gentle shaking (650 rpm on an IKA shaker MTS2). The reaction is stopped by the addition of 125 μl of ice-cold 5% TCA per well and incubated on ice for at least 30 minutes. The precipitate is transferred by harvesting onto filter plates (96-well microtitre filter plate: UniFilter-96, GF/B; Packard; No. 6005177), then washed four times with 1% TCA and dried at 60° C. After the addition of 35 μl scintillation solution (Ready-Safe; Beckmann) per well the plate is sealed shut with sealing tape and the amount of P33 precipitated is measured with the Wallac Betacounter. The measured data are evaluated using the standard Graphpad software (Levenburg-Marquard algorithm).

Measurement of Cytotoxicity on Cultivated Human Tumour Cells

To measure cytotoxicity on cultivated human tumour cells, cells of cervical carcinoma tumour cell line HeLa S3 (obtained from American Type Culture Collection (ATCC)) were cultivated in Ham's F12 Medium (Life Technologies) and 10% foetal calf serum (Life Technologies) and harvested in the log growth phase. Then the HeLa S3 cells were placed in 96-well plates (Costar) at a density of 1000 cells per well and incubated overnight in an incubator (at 37° C. and 5% $CO_2$), while on each plate 6 wells were filled with medium alone (3 wells as the medium control, 3 wells for incubation with reduced AlamarBlue reagent). The active substances were added to the cells in various concentrations (dissolved in DMSO; DMSO final concentration: 0.1%) (in each case as a triple measurement). After 72 hours incubation 20 μl AlamarBlue reagent (AccuMed International) were added to each well, and the cells were incubated for a further 7 hours. As a control, 20 μl reduced AlamarBlue reagent was added to each of 3 wells (AlamarBlue reagent, which was autoclaved for 30 min). After 7 h incubation the colour change of the Alamar-Blue reagent in the individual wells was determined in a Perkin Elmer fluorescence spectrophotometer (excitation 530 nm, emission 590 nm, slits 15 nm, integration time 0.1 ms). The amount of AlamarBlue reagent reacted represents the metabolic activity of the cells. The relative cell activity was calculated as a percentage of the control (HeLa S3 cells without inhibitor) and the active substance concentration which inhibited the cell activity by 50% (IC50) was derived. The values were calculated from the average of three individual measurements—with correction of the dummy value (medium control).

FACS Analysis

Propidium iodide (PI) binds stoichiometrically to double-stranded DNA, and is thus suitable for determining the proportion of cells in the G1, S, and G2/M phase of the cell cycle on the basis of the cellular DNA content. Cells in the G0 and G1 phase have a diploid DNA content (2N), whereas cells in the G2 or mitosis phase have a 4N DNA content.

For PI staining, for example, 0.4 million HeLa S3 cells were seeded onto a 75 cm$^2$ cell culture flask, and after 24 h either 0.1% DMSO was added as control or the substance was added in various concentrations (in 0.1% DMSO). The cells were incubated for 24 h with the substance or with DMSO before the cells were washed 2× with PBS and then detached with trypsin/EDTA. The cells were centrifuged (1000 rpm, 5 min, 4° C.), and the cell pellet was washed 2× with PBS before the cells were resuspended in 0.1 ml PBS. Then the cells were fixed with 80% ethanol for 16 hours at 4° C. or alternatively for 2 hours at −20° C. The fixed cells (10$^6$ cells) were centrifuged (1000 rpm, 5 min, 4° C.), washed with PBS and then centrifuged again. The cell pellet was resuspended in 0.25% Triton X-100 in 2 ml PBS, and incubated on ice for 5 min before 5 ml PBS were added and the mixture was centrifuged again. The cell pellet was resuspended in 350 μl PI staining solution (0.1 mg/ml RNase A, 10 μg/ml propidium iodide in 1×PBS). The cells were incubated for 20 min in the dark with the staining buffer before being transferred into sample measuring containers for the FACS scan. The DNA measurement was carried out in a Becton Dickinson FACS Analyzer, with an argon laser (500 mW, emission 488 nm), and the DNA Cell Quest Programme (BD). The logarithmic PI fluorescence was determined with a band-pass filter (BP 585/42). The cell populations in the individual cell cycle phases were quantified using the ModFit LT Programme made by Becton Dickinson.

The compounds according to the invention were also tested accordingly for other tumour cells. For example, these compounds are effective on carcinomas of many different kinds of tissue (e.g. breast (MCF7); colon (HCT116), head and neck (FaDu), lung (NCI-H460), pancreas (BxPC-3) and prostate (DU145)), sarcomas (e.g. SK-UT-1B), leukaemias and lymphomas (e.g. HL-60; Jurkat, THP-1) and other tumours (e.g. melanomas (BRO), gliomas (U-87MG)) and could be used for such indications. This is evidence of the broad applicability of the compounds according to the invention for the treatment of many different kinds of tumour types.

The compounds of general formula (I) may be used on their own or in conjunction with other active substances according to the invention, optionally also in conjunction with other pharmacologically active substances. Suitable preparations include for example tablets, capsules, suppositories, solutions, particularly solutions for injection (s.c., i.v., i.m.) and infusion, elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

In another aspect the present invention relates to pharmaceutical formulations, preferably pharmaceutical formulations of the type described above, characterised in that they contain one or more compounds of general formula (I).

The formulation examples which follow illustrate the present invention without restricting its scope:

EXAMPLES OF PHARMACEUTICAL FORMULATIONS

A)

| Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B)

| Tablets | per tablet |
|---|---|
| active substance | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

C)

| Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

What is claimed:
1. A compound of the formula

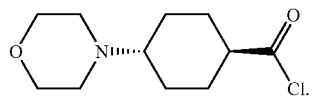

* * * * *